United States Patent
Liang et al.

(10) Patent No.: US 9,402,569 B2
(45) Date of Patent: Aug. 2, 2016

(54) SYSTEM AND/OR METHOD FOR GLUCOSE SENSOR CALIBRATION

(75) Inventors: Bradley Liang, Bloomfield Hills, MI (US); Kenneth W. Cooper, Newhall, CA (US); Raghavendhar Gautham, Los Angeles, CA (US); Rajiv Shah, Rancho Palos Verdes, CA (US); Keith Nogueira, Northridge, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 400 days.

(21) Appl. No.: 13/239,265

(22) Filed: Sep. 21, 2011

(65) Prior Publication Data

US 2012/0108933 A1  May 3, 2012

Related U.S. Application Data

(60) Provisional application No. 61/407,879, filed on Oct. 28, 2010.

(51) Int. Cl.
| | |
|---|---|
| *A61B 5/145* | (2006.01) |
| *A61B 5/00* | (2006.01) |
| *A61B 5/1486* | (2006.01) |
| *A61B 5/1495* | (2006.01) |

(52) U.S. Cl.
CPC ........... *A61B 5/14532* (2013.01); *A61B 5/0002* (2013.01); *A61B 5/1495* (2013.01); *A61B 5/14503* (2013.01); *A61B 5/14865* (2013.01); *A61B 5/6849* (2013.01); *A61B 5/7239* (2013.01); *A61B 2560/0214* (2013.01); *A61B 2560/0223* (2013.01)

(58) Field of Classification Search
CPC ............. A61B 5/14532; A61B 5/0002; A61B 5/14503; A61B 5/6849; A61B 5/14865; A61B 5/1495; A61B 5/7239; A61B 2560/0214; A61B 2560/0223
USPC .......................... 600/365, 322, 316, 367, 366
See application file for complete search history.

(56) References Cited

U.S. PATENT DOCUMENTS

| | | | |
|---|---|---|---|
| 4,562,751 A | 1/1986 | Nason | |
| 4,573,994 A | 3/1986 | Fischell | |
| 4,678,408 A | 7/1987 | Nason | |
| 4,685,903 A | 8/1987 | Cable | |
| 5,126,952 A * | 6/1992 | Kildal-Brandt et al. | ........ 702/91 |
| 5,299,571 A | 4/1994 | Mastrototaro | |
| 5,390,671 A | 2/1995 | Lord | |
| 5,391,250 A | 2/1995 | Cheney | |
| 5,482,473 A | 1/1996 | Lord | |
| 5,586,553 A | 12/1996 | Halili | |
| 5,951,521 A | 9/1999 | Mastrototaro | |
| 5,954,643 A | 9/1999 | VanAntwerp | |
| 6,360,888 B1 | 3/2002 | McIvor | |
| 6,368,141 B1 | 4/2002 | Antwerp | |
| 7,324,012 B2 | 1/2008 | Mann | |
| 2002/0035318 A1* | 3/2002 | Mannheimer et al. | ........ 600/323 |
| 2002/0161288 A1* | 10/2002 | Shin et al. | ..................... 600/316 |

* cited by examiner

*Primary Examiner* — Michael Kahelin
*Assistant Examiner* — Tho Tran
(74) *Attorney, Agent, or Firm* — Berkeley Law & Technology Group, LLP

(57) ABSTRACT

The subject matter disclosed herein relates to systems, methods and/or devices for calibrating sensor data to be used in estimating a blood glucose concentration. A relationship between sensor signal values and reference readings may be used to estimate a relationship between sensor signal values and measurements of blood glucose concentration.

12 Claims, 16 Drawing Sheets

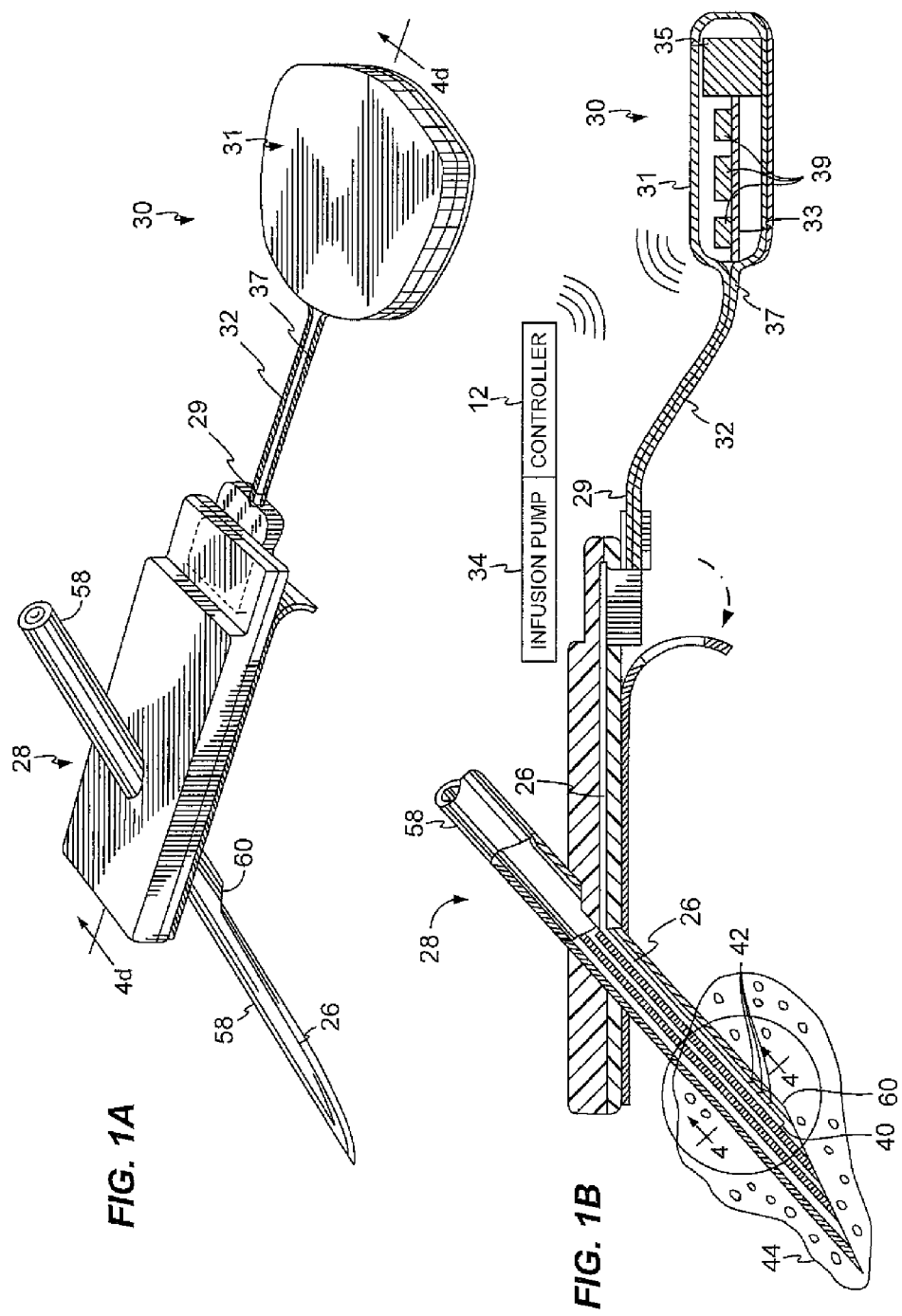

SYSTEM AND/OR METHOD FOR GLUCOSE SENSOR CALIBRATION

This application claims priority under 35 USC 119 to U.S. Provisional Application Ser. No. 61/407,879, filed Oct. 28, 2010, and entitled "System and/or Method for Glucose Sensor Calibration," which is assigned to the assignee hereof and which is incorporated herein by reference.

BACKGROUND

1. Field

The subject matter disclosed herein relates to calibration of glucose sensors for use in glucose monitoring systems, for example.

2. Information

Over the years, body characteristics have been determined by obtaining a sample of bodily fluid. For example, diabetics often test for blood glucose levels. Traditional blood glucose determinations have utilized a painful finger prick using a lancet to withdraw a small blood sample. This results in discomfort from the lancet as it contacts nerves in subcutaneous tissue. The pain of lancing and the cumulative discomfort from multiple needle pricks at least partially explains why patients fail to comply with a medical testing regimen used to determine a change in a body characteristic over a period of time. Although non-invasive systems have been proposed, or are in development, none to date have been commercialized that are effective and provide accurate results. In addition, all of these systems are designed to provide data at discrete points and do not provide continuous data to show the variations in the characteristic between testing times.

A variety of implantable electrochemical sensors have been developed for detecting and/or quantifying specific agents or compositions in a patient's blood. For instance, glucose sensors are being developed for use in obtaining an indication of blood glucose levels in a diabetic patient. Such readings are useful in monitoring and/or adjusting a treatment regimen which typically includes a regular administration of insulin to the patient. Thus, blood glucose readings improve medical therapies with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994. Typical thin film sensors are described in commonly assigned U.S. Pat. Nos. 5,390,671; 5,391,250; 5,482,473; and 5,586,553. See also U.S. Pat. No. 5,299,571.

BRIEF DESCRIPTION OF THE FIGURES

Non-limiting and non-exhaustive features will be described with reference to the following figures, wherein like reference numerals refer to like parts throughout the various figures.

FIG. 1a is a perspective view of an example glucose sensor system for use in accordance with an embodiment.

FIG. 1b is a side cross-sectional view of a glucose sensor system of FIG. 1a for an embodiment.

SUMMARY

Figure 1C:
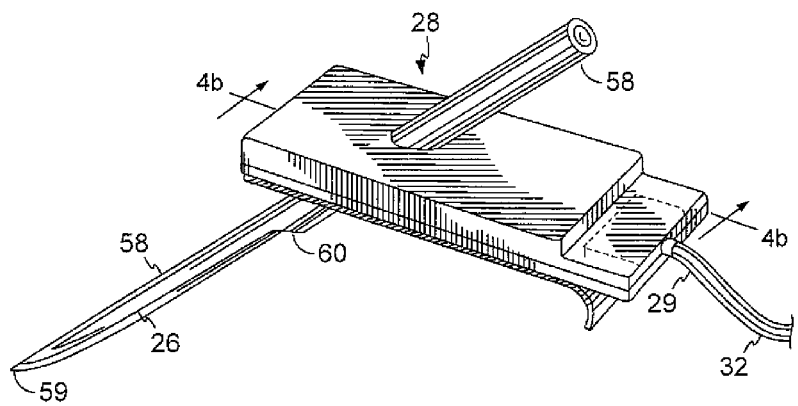
FIG. 1c is a perspective view of an example sensor set for a glucose sensor system of FIG. 1a for use in accordance with an embodiment.
Figure 1D:
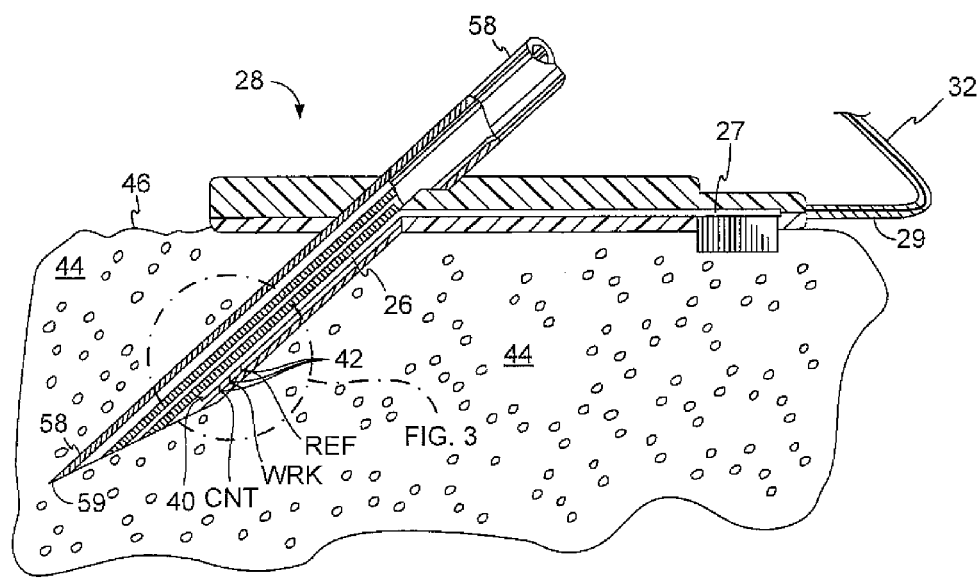
FIG. 1d is a side cross-sectional view of a sensor set of FIG. 1c for an embodiment.

Briefly, example embodiments may relate to methods, systems, apparatuses, and/or articles, etc. for obtaining a sequence of blood glucose reference measurements from a patient; and deriving a non-linear mapping between sensor signal values and measurements of blood glucose concentration in the patient based, at least in part, on temporal pairings of at least some of said blood glucose sensor reference measurements with said blood glucose sensor measurements signal values. In one particular implementation, the non-linear mapping may be derived, at least in part, as a piece-wise function comprising at least one linear portion and at least one non-linear portion. For example, the non-linear portion may be derived according to a polynomial expression. In yet another particular example, coefficients of terms in the polynomial expression may be based, at least in part, on the temporal pairings. In another particular example, the non-linear portion may be derived according to an exponential expression. Here, the exponential expression may be based, at least in part, on the temporal pairings. In another example implementation, for values in the non-linear portion, a measurement of blood glucose concentration may be obtained by applying an offset to a function defining the linear portion. In yet another alternative implementation, the non-linear relationship may comprise a cubic function and wherein deriving the non-linear relationship further comprises determining coefficients of the cubic function.

In another example implementation, an apparatus comprises a sensor to generate signal values responsive to a blood glucose concentration in a body; and a special purpose computing apparatus to: obtain a sequence of blood glucose reference measurements taken from the body; and derive a non-linear mapping between the signal values and measurements of blood glucose concentration in the body based, at least in part, on temporal pairings of at least some of the blood glucose reference measurements with the signal values. In another implementation, the non-linear relationship may be derived by deriving a piece-wise function comprising at least one linear portion and at least one non-linear portion. In another implementation, the special purpose computing apparatus may further obtain a measurement of blood glucose concentration by applying an offset to a function defining the linear portion for values in the non-linear portion. In yet another implementation, the non-linear relationship may comprise a cubic function, and the non-linear relationship is derived, at least in part, by determining coefficients of the cubic function.

In another example implementation, an article comprises a non-transitory storage medium having machine-readable instructions stored thereon which are executable by a special purpose computing apparatus to: obtain a sequence of blood glucose reference measurements taken from a body; and derive a non-linear mapping between sensor signal values and measurements of blood glucose concentration in said body based, at least in part, on temporal pairings of at least some of said blood glucose reference measurements with said sensor signal values. In an example implementation, the non-linear relationship may be derived by deriving a piece-wise function comprising at least one linear portion and at least one non-linear portion. In another implementation, the instructions may be further executable by the special purpose computing apparatus to obtain a measurement of blood glucose concentration by applying an offset to a function defining said linear portion for values in said non-linear portion. In yet another implementation, the non-linear relationship may comprise a cubic function, and wherein the non-linear relationship is derived, at least in part, by determining coefficients of the cubic function.

In yet another implementation, an apparatus comprises: means for obtaining a sequence of blood glucose reference measurements from a body; and means for deriving a non-linear mapping between sensor signal values and measurements of blood glucose concentration in said body based, at least in part, on temporal pairings of at least some of said blood glucose reference measurements with said sensor signal values. In one example implementation, the means for deriving said non-linear relationship may further comprise means for deriving a piece-wise function comprising at least one linear portion and at least one non-linear portion. In another example implementation, the non-linear portion is derived according to an exponential expression. In yet another example implementation, the apparatus further comprises means for determining parameters of said exponential expression based, at least in part, on said temporal pairings.

DETAILED DESCRIPTION

Reference throughout this specification to "one embodiment" or "an embodiment" means that a particular feature, structure, or characteristic described in connection with the embodiment is included in at least one embodiment of claimed subject matter. Thus, the appearances of the phrase "in one embodiment" or "an embodiment" in various places throughout this specification are not necessarily all referring to the same embodiment. Furthermore, the particular features, structures, or characteristics may be combined in one or more embodiments.

Systems for monitoring glucose in the body, for the treatment of diabetes for example, typically employ one or more glucose sensors to measure a blood-glucose concentration. For example, such sensors may be adapted to generate one or more electrical signals having a value (e.g., voltage and/or current level) that is related to such a blood-glucose concentration. Such a measurement of a blood-glucose concentration may then be used for any one of several applications such as, for example, monitoring a blood-glucose concentration for a diabetes patient.

Over time and/or with normal wear and usage of a glucose sensor, such a relationship between a value of a signal generated by the glucose monitoring blood sensor and actual measured blood glucose concentration may change. Accordingly, calibration of the signal generated by such a glucose monitoring with reference samples of blood-glucose concentration may enable an accurate estimate of a relationship between signal values generated by a glucose sensor and blood-glucose concentration in a patient, leading to more effective applications of glucose sensors and better treatment of diabetes patients.

As shown in the drawings for purposes of illustration, embodiments are directed to calibration methods for a glucose monitor that is coupled to a sensor set to provide continuous data recording of readings of glucose levels from a sensor for a period of time. In one particular implementation, a sensor and monitor provide a glucose sensor and a glucose monitor for determining glucose concentration levels in the blood and/or other bodily fluids of a user. However, it will be recognized that further embodiments may be used to observe concentration levels of other analytes, agents, compounds or compositions including, for example, hormones, cholesterol, medications concentrations, viral loads (e.g., HIV), bacterial levels, or the like without deviating from claimed subject matter. In particular implementations, a glucose sensor is primarily adapted for use in subcutaneous human tissue. However, in still further embodiments, one or more sensors may be placed in other tissue types, such as muscle, lymph, organ tissue, veins, arteries or the like, and used in animal tissue to measure body characteristics. Embodiments may record readings from the sensor on an intermittent, periodic, on-demand, continuous, or analog basis.

Briefly, in one particular embodiment, particular techniques for obtaining measurements of blood-glucose concentration have included application of a mathematical function or model to sensor signal values. For example, using sensor measurements paired with blood glucose sensor measurements (e.g., obtained from a test strip or other technique for obtaining blood glucose reference samples), a linear function may be derived based, at least in part, on a linear regression. The linear function may be updated from time to time in a calibration cycle to account for changes in sensor behavior from continued use as discussed above. In certain applications, however, a blood-glucose sensor may not provide signal values that accurately reflect actual blood glucose concentration according to a linear fashion. Use of a linear function, accordingly, may lead to inaccurate blood-glucose sensor measurements. In a closed-loop system for infusion of insulin, for example, employing a non-linear function to map sensor signal values to blood-glucose concentration measurements may significantly improve performance. In one particular embodiment, a non-linear relationship between estimates of blood glucose concentration in a patient and blood glucose sensor measurements is derived based, at least in part, on temporal pairings of at least some of said blood glucose sensor measurements with blood glucose reference measurements.

FIGS. 1a through 1d illustrate a glucose monitor system for use with calibration methods described herein. Such a glucose monitor system, in accordance with one particular implementation, includes a subcutaneous glucose sensor set 28 and a glucose monitor 30. Here, glucose monitor 30 may be of a type described in U.S. Pat. No. 7,324,012.

In one particular application, glucose monitor 30 may be worn by a user while connected to a surface mounted glucose sensor set 28 attached to the user's body by an electrically conductive cable 32. In one embodiment, a sensor interface may be configured in the form of a jack to accept different types of cables that provide adaptability of the glucose monitor 30 to work with different types of subcutaneous glucose sensors and/or glucose sensors placed in different locations of a user's body. However, in alternative embodiments, such a sensor interface may be permanently connected to cable 32. In additional alternative embodiments, a characteristic monitor may be connected to one or more sensor sets to record data of one or more body characteristics from one or more locations on or in a user's body.

According to an embodiment, glucose sensor set 28 may be of a type described in U.S. Patent Application Ser. No. 60/121,655, filed on Feb. 25, 1999, entitled "Glucose Sensor Set", or U.S. patent application Ser. No. 08/871,831, filed on Jun. 9, 1997, entitled "Insertion Set For A Transcutaneous Sensor." Glucose sensor 26 may be of a type described in U.S. patent application Ser. No. 09/101,218, filed on Feb. 25, 1999, entitled "Glucose Sensor", or described in commonly assigned U.S. Pat. Nos. 5,390,671; 5,391,250; 5,482,473; and 5,586,553; extends from the glucose sensor set 28 into a user's body with electrodes 42 of the glucose sensor 26 terminating in the user's subcutaneous tissue. See also U.S. Pat. No. 5,299,571. However, in alternative embodiments, glucose sensor 26 may use other types of sensors, such as chemical based, optical based, or the like. In further alternative embodiments, sensors may be of a type that is used on the external surface of the skin or placed below the skin layer of the user for detecting body characteristics. It should be understood, however, that these are merely examples types of sensors which may be used for monitoring a concentration of an analyte in bodily fluid, and that claimed subject matter is not limited in this respect.

According to an embodiment, glucose monitor 30 may be capable of recording and storing data as it is received from glucose sensor 2, and may include either a data port (not shown) or wireless transmitter and/or receiver (also not shown) for transferring data to and/or from a controller 12 such as a computer, communication station, a dedicated processor designed specifically to work with the glucose monitor, or the like. In a particular implementation, glucose monitor 30 may comprise a glucose monitor as described in U.S. Pat. No. 7,324,012. It should be understood, however, that this is merely an example glucose monitor for use in a particular embodiment, and that claimed subject matter is not limited in this respect.

In particular applications, a glucose monitor system may reduce inconvenience by separating complicated monitoring process electronics into two separate devices; the glucose monitor 30, which attaches to the glucose sensor set 28; and controller 12, which may contain the software and programming instructions to download and evaluate data recorded by glucose monitor 30. In addition, the use of multiple components (e.g., glucose monitor 30 and controller 12) may facilitate upgrades or replacements, since one module, or the other, can be modified, re-programmed, or replaced without requiring complete replacement of a monitor system. Further, the use of multiple components can improve the economics of manufacturing, since some components may require replacement on a more frequent basis, sizing requirements may be different for each module, different assembly environment requirements, and modifications can be made without affecting the other components.

Glucose monitor 30 may take raw glucose sensor data from glucose sensor 26 and assess such sensor data in real-time and/or stores it for later processing or downloading to controller 12, which in turn may analyze, display, and log the received data. Controller 12 may utilize the recorded data from glucose monitor 30 to analyze and review a blood glucose history. In particular embodiments, glucose monitor 30 is placed into a com-station which facilitates downloading data to a personal computer for presentation to a physician. Software may be used to download such data, create a data file, calibrate the data, and display such data in various formats including charts, forms, reports, graphs, tables, lists and/or the like. In further embodiments, a glucose monitor system as described herein may be used in a hospital environment and/or the like.

In alternative embodiments, glucose monitor 30 may include at least portions of software described as contained within controller 12 above. Glucose monitor 30 may further contain software enabling calibration of glucose sensor signals, display of a real-time blood glucose value, a showing of blood glucose trends, activate alarms and the like. A glucose monitor with these added capabilities may be useful for patients that might benefit from real-time observations of their blood glucose characteristics even while they're not in close proximity to a computer, communication device and/or dedicated independent data processor.

Controller 12 may include a display (not shown) adapted to display calculated results of raw glucose sensor data received via a download from glucose monitor 30. Results and information displayed may include, but not necessarily be limited to, trending information of a characteristic (e.g., rate of change of glucose), graphs of historical data, average characteristic levels (e.g., glucose), stabilization and calibration values, raw data, tables (showing raw data correlated with the date, time, sample number, corresponding blood glucose level, alarm messages, and more) and/or the like. Such a display may also be used in conjunction with buttons (not shown) on controller 12, computer, communication station, characteristic monitor and/or or the like, to program or update data.

Glucose monitor 30 may be combined with other medical devices to accept other patient data through a common data network and/or telemetry system. Glucose monitor 30 may be combined with a blood glucose meter to directly import or correlate glucose calibration reference values. Glucose monitor 30 may also be combined with semi-automated medication infusion pumps of the external type, as described according to particular embodiments in U.S. Pat. Nos. 4,562,751; 4,678,408; and 4,685,903; or automated implantable medication infusion pumps, as described according to particular embodiments in U.S. Pat. No. 4,573,994. Glucose monitor 30 may record data from the infusion pumps and/or may process data from both the glucose sensor 26 and an infusion pump to establish a closed loop system to control the infusion pump based, at least in part, on glucose sensor measurements. In other embodiments, other body characteristics are monitored, and the monitor may be used to provide feedback in a closed loop system to control a drug delivery rate. In further alternative embodiments, glucose monitor 30 can be combined with a glucose sensor set 28 as a single unit.

Glucose sensors may be replaced periodically to avoid infection, decaying enzyme coating and therefore sensor sensitivity, deoxidization of the electrodes, and/or the like. Here, a user may disconnect glucose sensor set 28 from cable 32 and glucose monitor 30. A needle 58 may be used to install another glucose sensor set 28, and then the needle 58 may be removed. Further description of the needle 58 and sensor set 28 according to particular embodiments may be found in U.S. Pat. Nos. 5,586,553; 6,368,141 and 5,951,521.

An initial reading may be downloaded from the glucose sensor set 10 and glucose monitor 30 to controller 12, to verify proper operation of glucose sensor 26 and glucose monitor 30. In particular embodiments, glucose sensor set 28 may provide data to glucose monitor 30 for one to seven days before replacement. Glucose sensor 26 may last in the user's body for longer or shorter periods of time depending on the quality of the installation, cleanliness, the durability of the enzyme coating, deoxidization of the sensor, user's comfort, and the like.

After installation into the body, glucose sensor 26 may be initialized to achieve a steady state of operation before starting a calibration process (e.g., for determining a function mapping sensor sample values with blood-glucose concentration measurements as discussed throughout).

The use of an initialization process can reduce the time for glucose sensor 26 stabilization from several hours to an hour or less, for example. One particular initialization procedure uses a two step process. First, a high voltage (e.g., between 1.0-1.1 volts—although other voltages may be used) may be applied between electrodes 42 of the sensor 26 for one to two minutes (although different time periods may be used) to allow sensor 26 to stabilize. Then, a lower voltage (e.g., between 0.5-0.6 volts—although other voltages may be used) may be applied for the remainder of the initialization process (e.g., 58 minutes or less). Other stabilization/initialization procedures using differing currents, currents and voltages, different numbers of steps, or the like, may be used. Other embodiments may omit such an initialization/stabilization process, if not required by a particular body characteristic sensor or if timing is not a factor. Alternatively, a characteristic monitor or controller 12 may apply an algorithm to the sensor data to determine whether initial transients have sufficiently diminished and the sensor is at a significantly stable state to begin calibration.

In particular embodiments, data may not be considered valid until a sensor initialization event flag (ESI) is set in data indicating that stabilization is complete. In one particular implementation, stabilization may be determined to be complete after 60 minutes or in response to a user setting a sensor initialization flag using one or more buttons on the glucose monitor 30. Following completion of stabilization/initialization, glucose monitor 30 may be calibrated to accurately interpret readings from the newly installed glucose sensor 26.

Beginning with the stabilization process, glucose monitor 30 may measure a continuous electrical current signal (ISIG) generated by glucose sensor 26 in connection with a concentration of glucose present in the subcutaneous tissue of the user's body. In particular embodiments, glucose monitor 30 may sample the ISIG from glucose sensor 26 at a sampling rate of once every 10.0 seconds, for example, as shown in FIGS. 2a-c. Examples of sampled values are labeled A-AD in FIG. 2a. At an interval rate of once per minute, the highest and lowest of the sampled values (shown in FIG. 2a as circled sampled values A, E, G, I, M, R, V, W, Y, and AB) are ignored, and the remaining four sampled values from an interval are averaged to create interval values (shown in FIG. 2b as values F', L', R', X', and AD'). At a glucose monitor memory storage rate of once every five minutes, the highest and lowest of the interval values (shown in FIG. 2b as values L' and X') are ignored and the remaining three interval values are averaged and stored in a glucose monitor memory as memory values (shown in FIG. 2c as point AD"). The internal values may be retained in memory and may be downloaded to controller 12. Such interval values may be used to calibrate glucose monitor 30 and/or controller 12 and to analyze blood glucose levels. The sampling rate, interval rate and the memory storage rate may be varied as desired to capture data with sufficient resolution to observe transients or other changes in the data depending on the rate at which sensor values can change, which is affected by the sensor sensitivity, the body characteristic being measured, the physical status of the user, and the like. In other embodiments, all of the sampled values may be included in the average calculations of memory storage values. In alternative embodiments, more or less sampled values or interval values are ignored depending on the signal noise, sensor stability, or other causes of undesired transient readings. Finally, in still other embodiments, all sampled values and/or interval values may be stored in memory.

Clipping limits may be used to limit a signal magnitude variation from one value to the next thereby reducing the effects of extraneous data, outlying data points, or transients. In particular embodiments, clipping limits may be applied to interval values. For instance, interval values that are above a maximum clipping limit or below a minimum clipping limit may be replaced with the nearest clipping limit value.

In alternative embodiments, interval values that are outside of clipping limits may be ignored and not used to calculate a subsequent memory storage value. In particular implementations, detection of interval values outside of clipping limits may be considered a calibration cancellation event. In further particular embodiments, a calibration cancellation event may be recognized if more than one value is deemed outside of clipping limits.

In particular embodiments, clipping limits may be shifted after each data point. Here, clipping limits may be set to a level based, at least in part, on an acceptable amount of change from a previous interval value to a present interval value, which is affected by sensor sensitivity, signal noise, signal drift, and/or the like. In particular implementations, clipping limits may be calculated for a current interval based on the magnitude of the previous interval value. For example, for a previous interval value from zero up to but not including 15.0 Nano-Amps, clipping limits may be set at plus and minus 0.5 Nano-Amps about the previous interval value. For a previous interval value from 15.0 Nano-Amps up to but not including 25.0 Nano-Amps, clipping limits may be set at plus and minus 3% of the previous interval value, about the previous interval value. For a previous interval value from 25.0 Nano-Amps up to but not including 50.0 Nano-Amps, clipping limits may be set at plus and minus 2% of the previous interval value, about the previous interval value. For a previous interval value of 50.0 Nano-Amps and greater, clipping limits may be set at plus and minus 1% about the previous interval value. In alternative embodiments, different clipping limits may be used and claimed subject matter is not limited in this respect.

Figure 3:
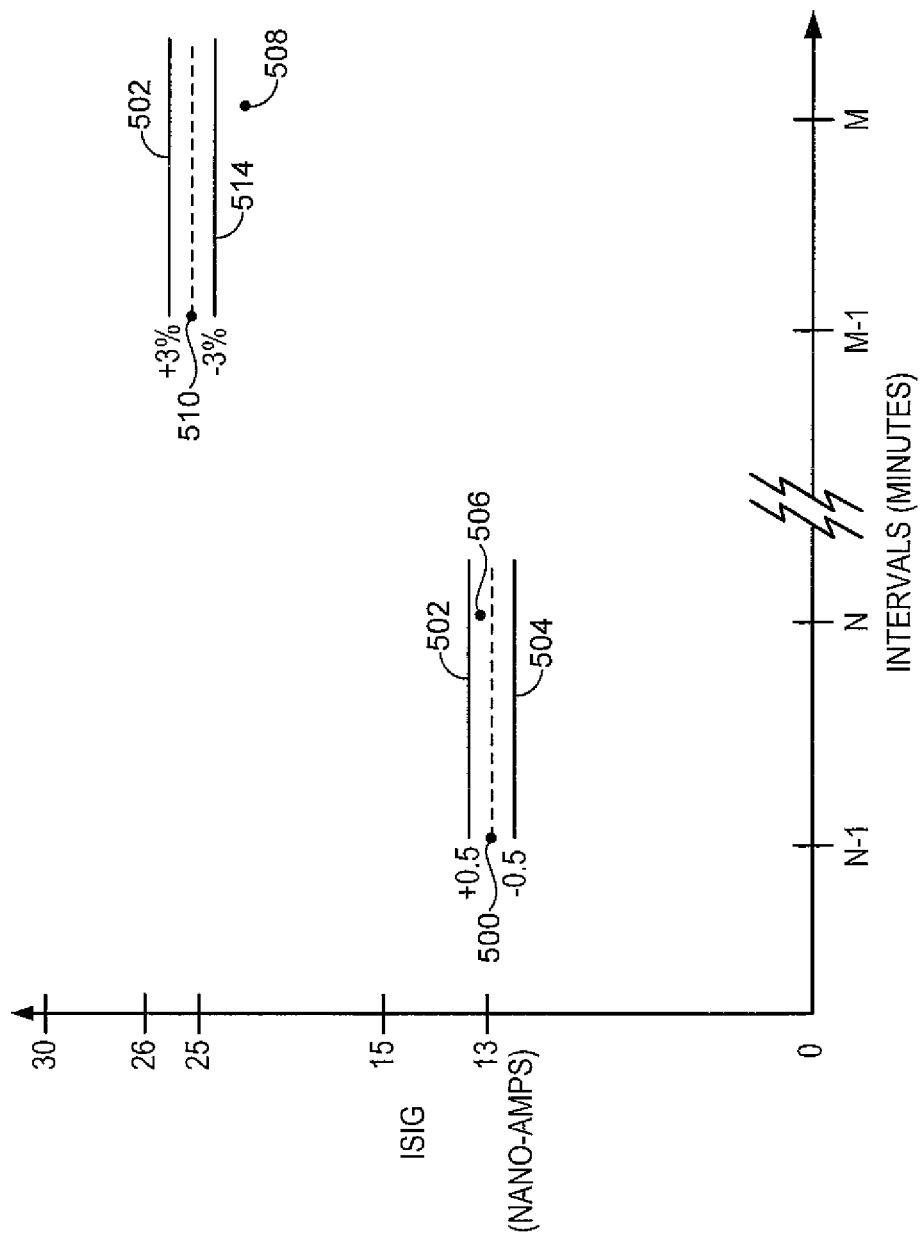
FIG. 3 is a chart showing clipping limits according to an embodiment.

FIG. 3 shows a clipping limit example according to a particular embodiment in which a previous interval value 500, associated with interval N−1, has a magnitude of 13.0 Nano-Amps, which is less than 15.0 Nano-Amps. Therefore, an upper clipping limit 502 for a present interval value 506 is set at 13.5 Nano-Amps, which is 0.5 Nano-Amps greater than the magnitude of the previous interval value 500. A lower clipping limit 504 is set at 12.5 Nano-Amps which is 0.5 Nano-Amps below the previous interval value 500. Present interval value 506, associated with interval N, is between the upper clipping limit 502 and the lower clipping limit 504 and is therefore acceptable.

In another example shown in FIG. 3, the present interval value 508, associated with interval M, has a value of 25.0 Nano-Amps which is outside of the clipping limit 514 and will therefore be clipped. The previous interval value 510, associated with interval M−1, is 26.0 Nano-Amps, which is included in the range from 25.0 up to but not including 50.0 Nano-Amps as discussed above. Therefore the clipping limits are +/−2%. The maximum clipping limit 512 is 2% greater than the previous interval value 510 as follows:

26.0+26.0*0.02=26.5 Nano-Amps.

Similarly the minimum clipping limit 514 is 2% less than the previous interval value 510 as follows:

26.0−26.0*0.02=22.5 Nano-Amps.

Figure 2:
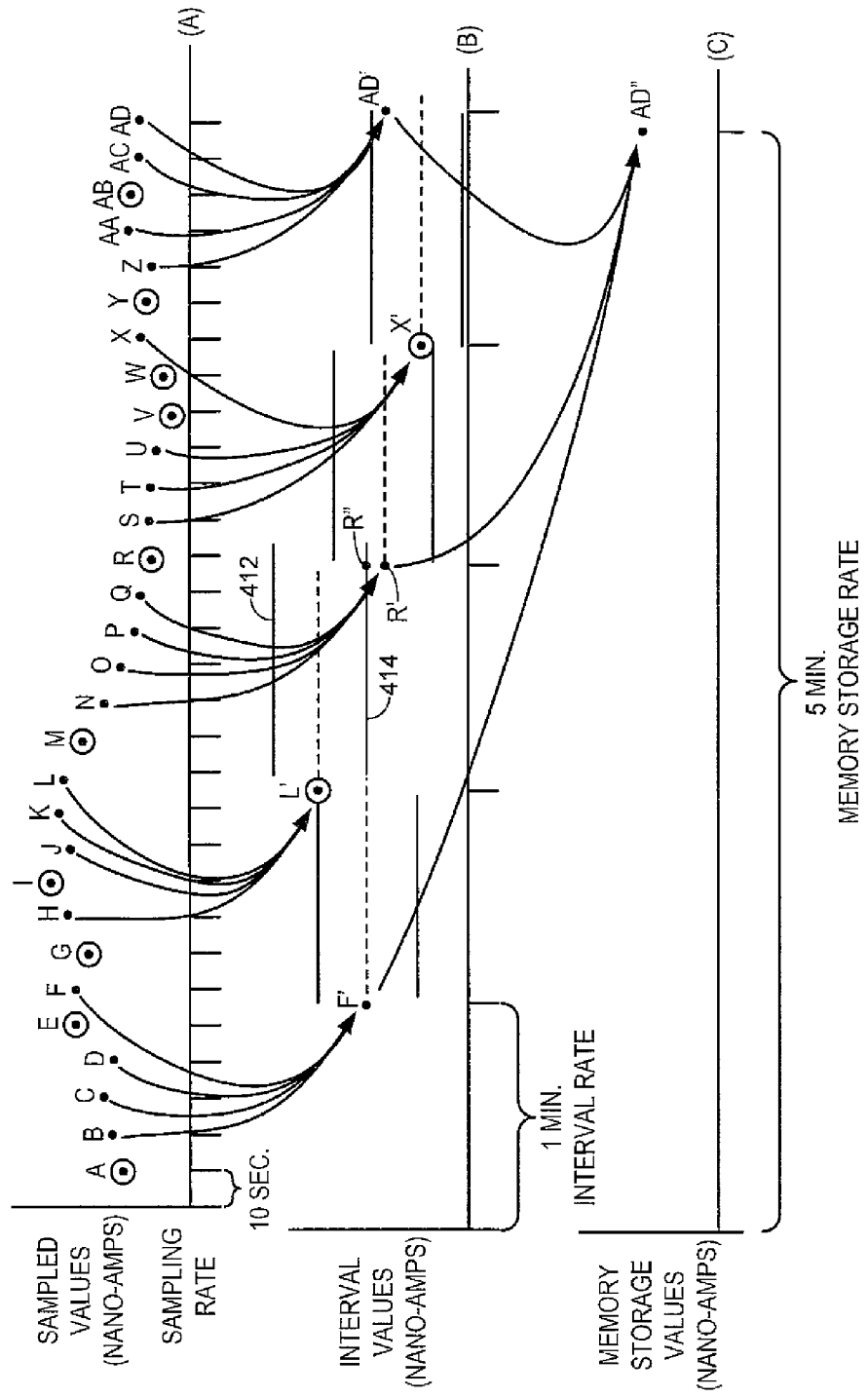
FIGS. 2a through 2c are diagrams showing a relationship between sampled values, interval values and memory storage values according to an embodiment.

Since the present interval value 508 of 25.0 Nano-Amps is less than the minimum clipping limit 514 of 25.5 Nano-Amps, it will be clipped, and 25.5 Nano-Amps will be used in place of 25.0 Nano-Amps to calculate a memory storage value. For further illustration, FIG. 2 shows interval value R', which is calculated by averaging sampled values N through Q, is outside of the clipping limits 412 and 414, which result from the previous interval value U. Therefore, in this particular example, the magnitude of interval value R is not used to calculate memory value AD″, instead R″, which is the magnitude of the minimum clipping limit 414, is used.

In other embodiments, clipping limits may be a smaller or larger number of Nano-Amps or a smaller or larger percentage of the previous interval value based on the sensor characteristics mentioned above. Alternatively, clipping limits may be calculated as plus or minus the same percent change from every previous interval value. Other algorithms may use several interval values to extrapolate the next interval value and set the clipping limits to a percentage higher and lower than the next anticipated interval value. In further alternatives, clipping may be applied to the sampled values, interval values, memory values, calculated glucose values, estimated values of a measured characteristic, or any combination of such values.

In particular embodiments, interval values are compared to an out-of-range limit of 200.0 Nano-Amps. If three consecutive interval values are equal to or exceed the out-of-range limit, the sensor sensitivity may be deemed to be too high, and an alarm is activated to notify the user that re-calibration is required or the sensor may need replacing. In alternative embodiments, an out-of-range limit may be set at higher or lower values depending on the range of sensor sensitivities, the expected working life of the sensor, the range of acceptable measurements, and/or the like. In particular embodiments, an out-of range limit is applied to sampled values. In other embodiments, an out-of-range limit is applied to the memory storage values.

In particular embodiments, unstable signal alarm limits may be set to detect drastic changes in memory storage values from one to another. Signal alarm limits may be established similarly to the clipping limits described above for the interval values, but allow for a larger change in value since there is more time between memory storage values than between interval values. Re-calibration or replacement of the glucose sensor 26 may be performed once an unstable signal alarm is activated. In essence, in a particular implementation, such an alarm is therefore activated in the event that glucose monitor 30 detects an unacceptable level of noise in the ISIG from glucose sensor 26.

In a particular embodiment, a memory storage value may be considered valid (Valid ISIG value) unless one of the following calibration cancellation events occurs: an unstable signal alarm; a sensor initialization event; a sensor disconnect alarm; a power on/off event; an out-of-range alarm; or a calibration error alarm. Here, only Valid ISIG values may be used to calculate blood glucose levels by the glucose monitor 30 or controller 32. Once a calibration cancellation event occurs, successive memory storage values are not valid, and therefore are not used to calculate blood glucose, until glucose monitor 30 or controller 32 is re-calibrated. If glucose monitor 30 is turned off for a short enough period of time, up to 30 minutes for example, memory storage values may be considered Valid ISIG values as soon as the power is restored. If the power is off for longer than 30 minutes, for example, glucose monitor 30 may be re-calibrated before ISIG values are considered valid. Alternatively, power may be off for a duration such as 30 minutes or longer and, once power is restored, the memory storage values may comprise Valid ISIG values. Here, a sensor disconnect alarm may be activated if the glucose monitor 30 does not detect a signal. In preferred embodiments, when two or more out of five interval values collected within a given memory storage rate are less than 1.0 Nano-Amp, a disconnect alarm may be triggered. In alternative embodiments, greater or fewer values need be below a particular threshold current level to trigger a disconnect alarm depending of the acceptable range or sensor readings and the stability of an associated sensor signal. Two remaining calibration cancellation events, the calibration error and an alternative embodiment for the out-of-range alarm, are discussed in conjunction with the calibration process below.

Particular implementations are directed to calibration techniques that may be used by either glucose monitors during real-time measurements of one or more signals from a glucose sensor, or post processors during post-processing of data that has been previously recorded and downloaded.

To calibrate glucose monitor 30, a function mapping sensor signal values (e.g., Valid ISIG values) to blood-glucose sensor measurements may be determined. As discussed above, such a function may comprise a non-linear function. A function mapping sensor signal values to blood-glucose sensor measurements may be based, at least in part, on a calibration factor called a sensitivity ratio (SR) (blood glucose level/ Valid ISIG value) calculated for a particular glucose sensor 26. SR may be used to measure/estimate a blood glucose concentration in certain cases based, at least in part on a Valid ISIG value (Nano-Amps) into a blood glucose level (mg/dl or mmol/l). In alternative embodiments, units for the SR may vary depending on a type of signal available from the sensor (frequency, amplitude, phase shift, delta, current, voltage, impedance, capacitance, flux, and the like), the magnitude of the signals, the units to express the characteristic being monitored, and/or the like.

Figure 4:
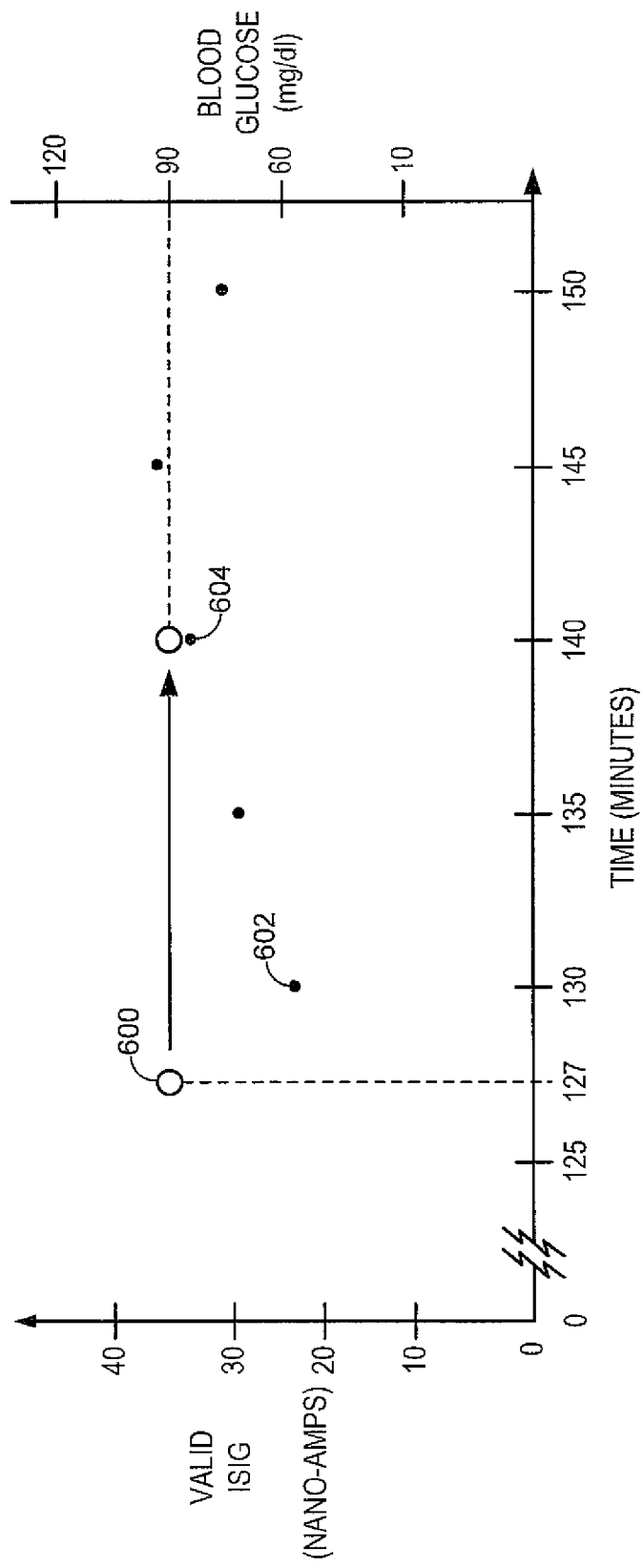
FIG. 4 is a chart illustrating the pairing of a blood glucose reference reading with glucose monitor data according to an embodiment.

In particular implementations, a user may obtain a blood glucose reference reading from a common glucose meter, or another blood glucose measuring device, and immediately enter such a blood glucose reference reading into glucose monitor 30. Such a blood glucose reference reading may be assumed to be accurate and therefore used as a reference for calibration. Glucose monitor 30, or a controller 12, may temporally correlate a blood glucose reference reading with a Valid ISIG value to establish a "paired calibration data point." Since a glucose level in an interstitial body fluid tends to lag behind a blood glucose level, glucose monitor 30 or controller 12 applies a delay time and then pairs the blood glucose reference reading with a Valid ISIG value as shown in FIG. 4. In particular embodiments, an empirically derived ten minute delay may be used. In a particular implementation where Valid ISIG values are averaged and stored every five minutes, glucose monitor 30 may correlate a blood glucose reference reading with the third Valid ISIG stored in memory after the blood glucose reference reading is entered (resulting in an effective delay of ten to fifteen minutes in this particular example). FIG. 4 illustrates an example, in which a blood glucose reference reading 600 of 90 mg/dl is entered into glucose monitor 30 at 127 minutes. The next Valid ISIG value 602 may be stored at 130 minutes. Given a 10 minute delay, a glucose reference reading 600 may be paired with Valid ISIG value 604 which is stored at 140 minutes with a value of 30 Nano-amps. We point out that two numbers may be used to establish one paired calibration data point, a blood glucose reference reading and a Valid ISIG.

Other delay times may be used depending on a particular user's metabolism, response time of the sensor, delay time incurred for the glucose meter to calculate a reading and for the reading to be entered into the glucose monitor 100, a type of analyte being measured, the tissue that the sensor is placed into, environmental factors, whether the previous glucose Valid ISIG value (or the trend of the Valid ISIG values) was higher or lower than current Valid ISIG value, and/or the like. Once paired calibration data is available, an appropriate calibration process may be applied depending, at least in part, on how many paired calibration data points are available since the last calibration, a total period of time that glucose sensor 26 has been in use, and a number of times glucose sensor 26 has been calibrated.

In particular embodiments, blood glucose reference readings may be entered into glucose monitor 30 periodically throughout each day of use. Here, calibration may be conducted immediately after the initialization/stabilization of glucose sensor 26 and once a day thereafter. However, such calibration may be conducted more or less often depending on whether glucose sensor 26 has been replaced, whether a calibration cancellation event has occurred, the stability of glucose sensor 26 sensitivity over time, and/or the like.

In example embodiments, blood glucose reference readings are collected several times per day but a new calibration factor is calculated only once per day. Therefore, typically more than one paired calibration data point is collected between calibrations. In alternative embodiments, the glucose monitor may be calibrated whenever a new paired calibration data point is collected.

Figure 5:
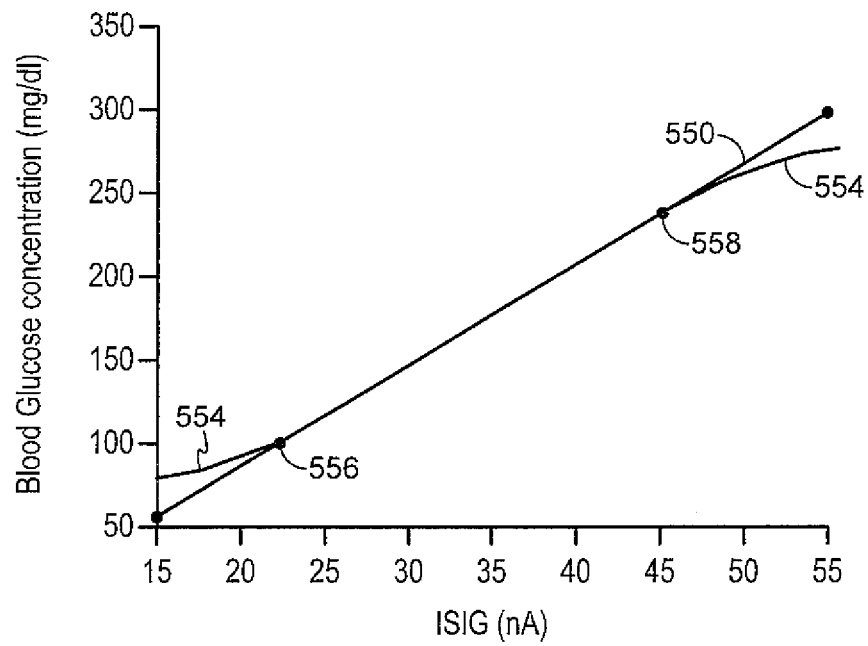
FIG. 5 is a plot of a relationship between glucose sensor signal values and blood glucose concentration approximated by a non-linear function according to an embodiment.

As discussed above, previous approaches to determining a relationship between sensor signal values and blood-glucose concentration have involved defining a linear function that maps sensor signal values to measurements of blood-glucose concentration. Through a calibration process using temporally correlated pairs of blood-glucose reference samples and sensor signal values, this linear function may be updated from time to time to account for changes in the sensor arising from normal wear, etc. FIG. 5 shows a plot of a linear function 550 that may be used to approximate blood-glucose concentration as a function of sensor signal values and a plot 554 of actual blood-glucose concentration at sensor signal values over a range. Here, it can be observed that, at least at higher and lower portions of the range of sensor signal values, the linear function 550 deviates significantly from plot 554. Similarly, in another embodiment shown in FIG. 6, a plot of a linear function 650 that may be used to approximate blood-glucose concentration as a function of sensor signal values deviates significantly from a plot 652 of actual blood-glucose concentration at least at a lower range.

In a particular embodiment, a non-linear function is determined for mapping sensor signal values to measurements of blood-glucose concentration. Here, such a non-linear function may derived and/or updated in a calibration process from temporally correlated pairs of blood-glucose reference samples and sensor signal values as described above. In one particular example, such a non-linear function may be derived as a polynomial function that attempts to fit a curve to a mapping of sensor signal values and actual blood-glucose concentration. For example, a calibration process may derive/estimate coefficients a, b, c and d of the following cubic function:

$$\text{blood-glucose sensor measurement} = a\text{ISIG}^3 + b\text{ISIG}^2 + c\text{ISIG} + d$$

In particular implementations, coefficients a, b, c and d may be derived or estimated based, at least in part, on temporal pairings of sensor signal values and blood-glucose reference measurements using any one of several polynomial curve fitting techniques known to those of ordinary skill in the art. It should be understood that this is merely an example polynomial function for use in mapping sensor signal values to blood-glucose sensor measurements and that claimed subject matter is not limited in this respect.

Alternatively, a calibration process may derive or estimate parameters e, f and g of the following exponential function for mapping sensor signal values to blood-glucose sensor measurements:

$$\text{blood-glucose sensor measurement} = (\text{ISIG} + e)^f + g.$$

In particular implementations, parameters e, f and g may be derived or estimated based, at least in part, on temporal pairings of sensor signal values and blood-glucose reference measurements using any one of several exponential curve fitting techniques known to those of ordinary skill in the art. Also, it should be understood that this is merely an example exponential function for use in mapping sensor signal values to blood-glucose sensor measurements and that claimed subject matter is not limited in this respect.

Figure 6:
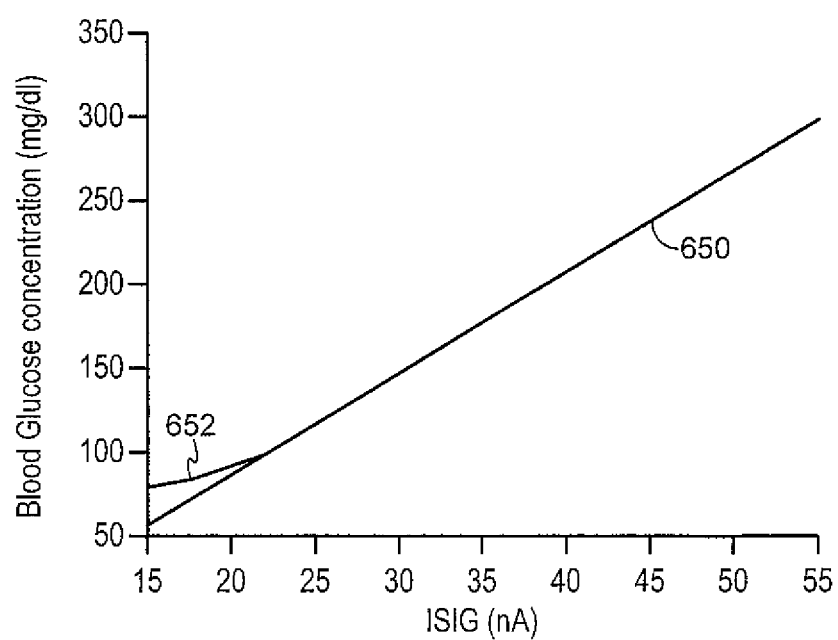
FIG. 6 is a plot of a relationship between glucose sensor signal values and blood glucose concentration approximated by a non-linear function according to an alternative embodiment.

In another implementation, a non-linear function may be derived and/or updated in a calibration process to provide a function that is linear in at least a portion where changes in sensor measurement values reflect changes in blood-glucose concentration in a substantially linear fashion. In observing the particular plot 554 of FIG. 5, for example, plot 554 substantially follows linear function 550 in the range of ISIG from about 22.5 nA to 45.0 nA. In the ranges of ISIG less than 22.5 nA and greater than 45.0 nA however, plot 554 deviates from linear function 550. Similarly, in observing the particular plot 652 of FIG. 6, plot 652 substantially follows linear function 650 in a region of ISIG above 22.5 nA. In the range of ISIG below 22.5 nA however, plot 652 substantially deviates from linear function 650. In these two examples, a portion of a function to map ISIG to blood glucose concentration in a range of ISIG in which the sensor responds to blood glucose concentration in a linear fashion (e.g., ISIG less than 22.5 nA and greater than 45.0 nA for the embodiment of FIG. 5 or ISIG above 22.5 nA for the embodiment of FIG. 6) and may be determined as a linear function defined by a calibration factor and offset as discussed below.

Figure 7:
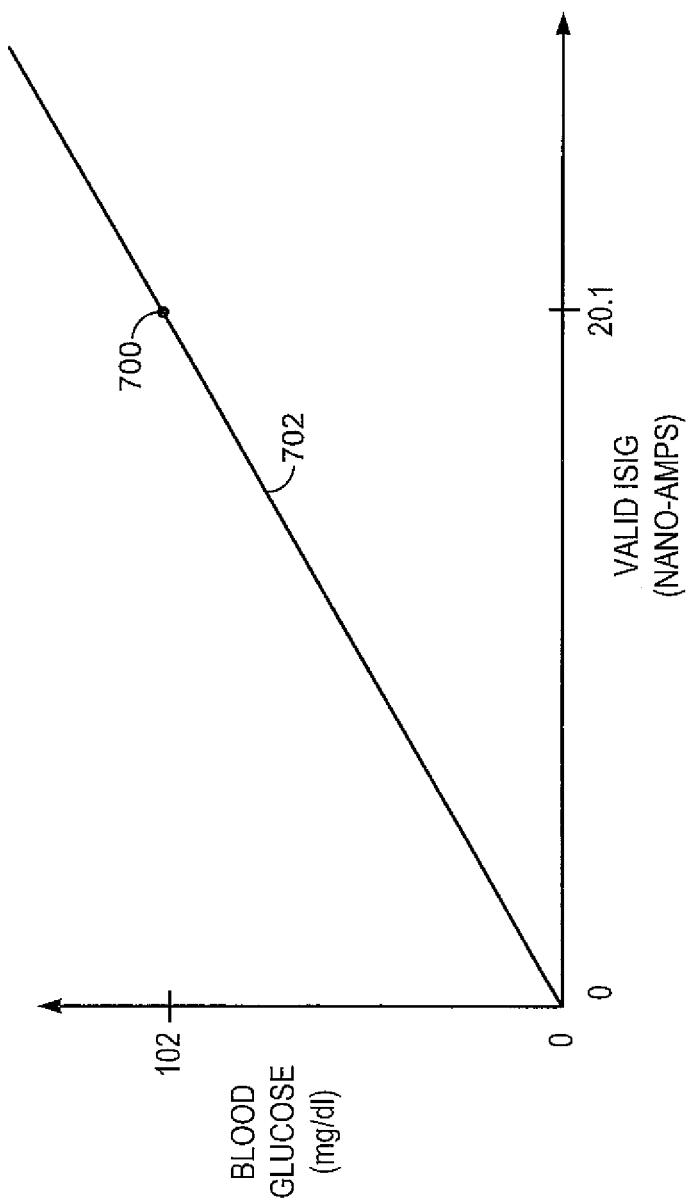
FIG. 7 is a chart illustrating an example of a single-point calibration according to an embodiment.

In one particular implementation, a function for mapping sensor signal values to blood-glucose concentration measurements may be determined by first determining a linear portion in particular ISIG ranges (e.g., the range of ISIG from 22.5 nA to 45.0 nA for FIG. 6 and above 22.5 nA for FIG. 7). Once such a linear portion is determined, portions in adjacent ranges of ISIG may be determined. For example, the function may be defined as a continuous function across a full range of ISIG where an endpoint of a linear portion (e.g., endpoint 556 or endpoint 558 in FIG. 5) defines an endpoint for an adjacent portion. Bounded by this endpoint, the adjacent portion may be determined using any one of several techniques. For example, such an adjacent portion may also be linear, but with a different slope/rate than that of the linear portion determined first (e.g., the range of ISIG from 22.5 nA to 45.0 nA for FIG. 6 and above 22.5 nA for FIG. 7).

In one particular implementation, a portion of a function for mapping sensor signal values to blood-glucose concentration measurements adjacent to a predetermined linear portion that deviates from the predetermined linear portion may be determined as a polynomial function of ISIG (e.g., as a cubic polynomial having the form $aISIG^3+bISIG^2+cISIG+d$) or exponential function (e.g., $(ISIG+e)^f+g$). As discussed above, coefficients or parameters for such a polynomial function may be determined using any one of several well known curve fitting techniques. For example, such a polynomial function or exponential function may be constrained to be fixed to aforementioned endpoints of linear portions of a function to maintain continuity.

In another particular implementation, such a portion of a function for mapping sensor signal values to blood-glucose concentration measurements adjacent to a predetermined linear portion may be determined according to an offset or deviation from a linear function. In the particular embodiment of FIG. 5, for example, a blood-glucose concentration measurement in a range for ISIG less than 22.5 nA may be determined as an offset value added (e.g., in units of mg/dl) to a corresponding value on a point along linear function 550. Likewise, a blood-glucose concentration measurement in a range for ISIG greater than 45.0 nA may be determined as an offset value subtracted (e.g., in units of mg/dl) from a corresponding value on a point along linear function 550.

In one particular implementation, a particular offset value to be added to or subtracted from a point along linear function 550 may be determined according to a look-up table. Here, indices for such a look-up table may include, for example, a slope and/or offset defining linear function 550. In the particular example embodiment of FIG. 5, a non-linear function mapping sensor signal values to blood-glucose concentration measurements may be expressed as follows:

$$SG_m = ISIGm + \text{offset, for } 22.5 \text{ nA} < ISIG < 45.0 \text{ nA};$$
$$= ISIGm + \text{offset} + LUT(m, ISIG, \text{offset}),$$
$$\text{for } ISIG < 22.5 \text{ or } ISIG > 45.0 \text{ nA}$$

where:
m is the slope of linear function 550;
offset is an offset or slope intercept of linear function 550;
$SG_m$ is a blood-glucose concentration measurement derived from a sensor signal value; and
LUT(m, ISIG, Offset) is a value selected from a look up table according to m, ISIG and Offset.

In particular implementations, a linear portion of a function mapping sensor signal measurements to blood-glucose concentration measurements may be determined using any one of several techniques. For example, such a linear portion may be defined by a slope or rate (e.g., as m defining a slope or rate for linear function 550), and an offset value (e.g., offset or slope intercept for linear function 550) using any one of several techniques discussed below. Such a slope or rate may comprise or be derived from a sensitivity ratio (SR) including a single-point sensitivity ratio (SPSR), a modified SPSR (MSPSR), linear regression sensitivity ration (LRSR) or a modified (MLRSR) using techniques described below, for example.

Figure 8:
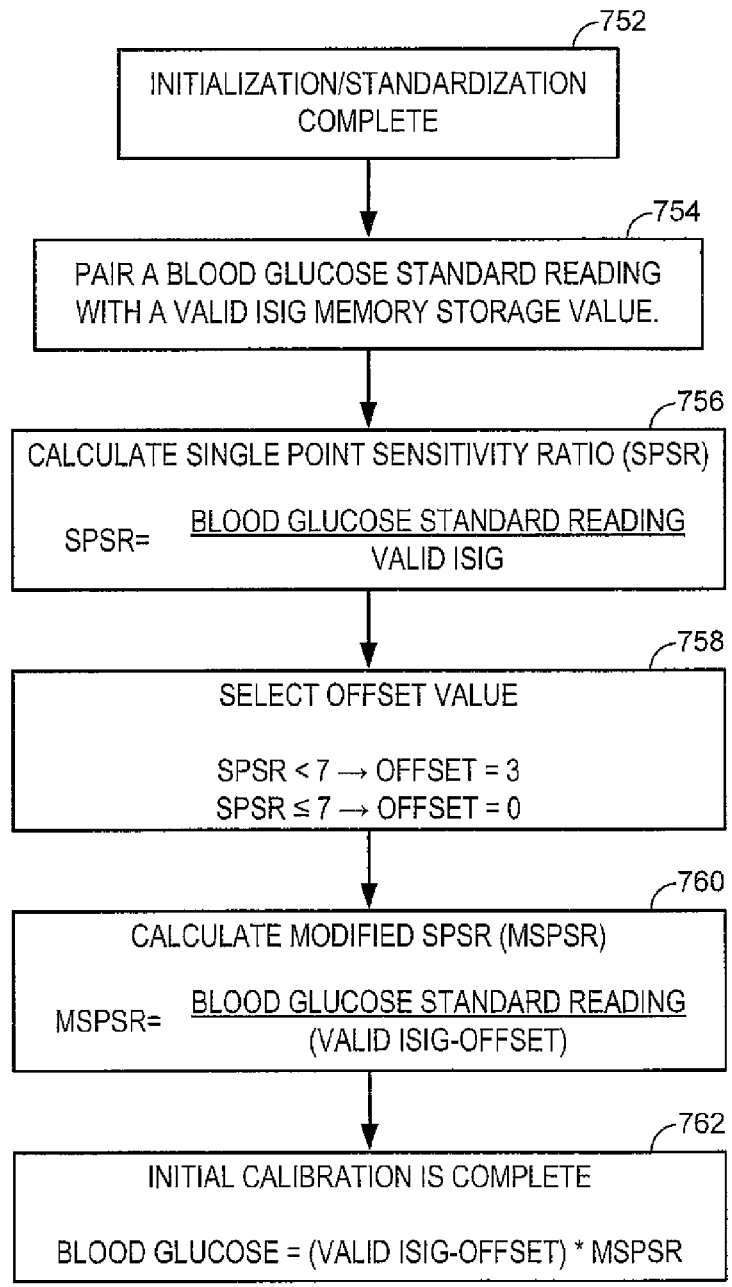
FIGS. 8 and 9 are flow diagrams illustrating an example of a linear regression calibration according to an embodiment.
Figure 9:
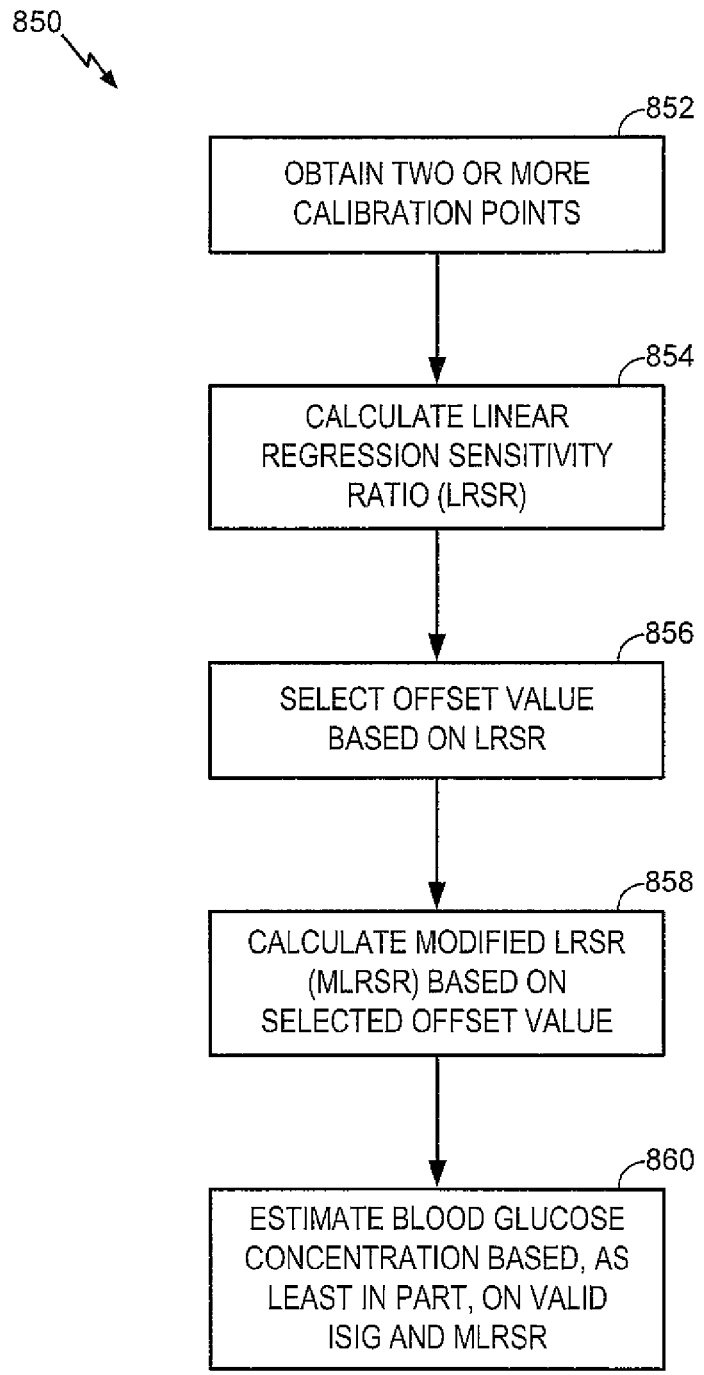

Particular embodiments may use a single-point calibration technique (e.g., as shown in FIG. 8) to calculate the SR if only a single paired calibration data point is available, such as immediately after initialization/stabilization. And a modified linear regression technique (shown in a block diagram in FIG. 9) may be used if two or more paired calibration data points are available. Particular embodiments may use a single-point calibration technique whether or not more than one paired calibration data point is available.

A single-point calibration equation may be based on an assumption that a Valid ISIG will be 0 when the blood glucose is 0. As shown in FIGS. 7 and 8, a single paired calibration point 700 obtained at block 754 is used with the point (0,0) to establish a line 702. The slope of the line from the origin (0,0) and passing through the single paired calibration point 700 provides a single-point sensitivity ratio (SPSR). Here, block 756 may calculate such an SPSR as follows:

$$SPSR = \frac{\text{Blood Glucose Reference Reading}}{\text{Valid } ISIG}$$

Therefore, the calibrated blood glucose level may be expressed as follows:

Blood Glucose Level=Valid ISIG*SPSR

As an example, using the values of 20.1 Nano-Amps and 102 mg/dl from the paired calibration data point shown in FIG. 8, calculation of SPSR may be expressed as follows:

SPSR=102/20.1=5.07 mg/dl per Nano-Amp

To continue with the current example, once calibration is complete, given a glucose sensor reading of 15.0 Nano-Amps, calculated blood glucose level may be determined as follows:

Blood Glucose Level=15.0*5.07=76.1 mg/dl

Additionally, particular embodiments may use an offset value in a calibration equation to compensate for the observation that more sensitive glucose sensors 12 (e.g., glucose sensors 12 that generate higher ISIG values compared to other glucose sensors 12 at the same blood glucose level, which result in lower SR values) may have a less linear performance at very high blood glucose levels in comparison to glucose sensors 12 with lower sensitivity (and therefore relatively higher SR values). If the SPSR for a particular glucose sensor 12, as calculated above, is less than a sensitivity threshold value, then a modified SPSR (MSPSR) may be calculated at block 760 using an offset value selected at block 758. In one particular implementation, the threshold value is 7.0 mg/dl per nA. If the initial calculation of the SPSR (shown above) is less than 7.0 mg/dl per nA, for example, an offset value of 3.0 mg/dl may be used to calculate the MSPSR. If the initial calculation of SPSR yields a value of 7.0 mg/dl per nA or greater, then the offset value may be 0.0 mg/dl. Thus, the MSPSR may be calculated at block 760 using the offset value according to a modified single-point calibration expression, as follows:

$$MSPSR = \frac{\text{Blood Glucose Refrence Reading}}{\text{Valid } ISIG - \text{offset}}$$

Accordingly, an initial calibration of sensor 12 may be used to estimate a blood glucose from a sensor measurement at block 762 as follows:

Blood Glucose Level=(Valid ISIG−offset)*SPSR

Continuing the above example since the SPSR is 5.07 mg/dl per nA, which is less than 7.0 mg/dl per nA, the sensitivity ratio is recalculated using the MSPSR equation as:

MSPSR=102/(20.1−3)=5.96 mg/dl per Nano-Amp

Given a glucose sensor reading of 15.0 Nano-Amps after calibration, the calculated blood glucose may be expressed as follows:

Blood Glucose Level=(15.0−3)=5.96=71.5 mg/dl

In another example, given a blood glucose reference reading of 95.0 mg/dl from a typical blood glucose meter and a Valid ISIG value of 22.1 nA, a resulting SPSR may be determined as 95/22.1=4.3. Since SR<7.0 mg/dl per nA, the offset=3.0 mg/dl. Therefore, the MSPSR is 95/[22.1−3]≈5.0 mg/dl per nA. Note that if the SPSR is greater than or equal to 7.0 mg/dl per nA the offset value is 0.0 mg/dl and therefore the MSPSR=SPSR.

In alternative embodiments, the offset value may be eliminated from the expression for calculating the blood glucose value as follows:

Blood Glucose Level=Valid ISIG*MSPSR

The threshold value of 7.0 mg/dl per nA and the associated offset of 3.0 mg/dl have been empirically selected based on the characteristics observed from testing a particular type of glucose sensors 12, such as those described in U.S. Pat. No. 5,391,250 entitled "Method of Fabricating Thin Film Sensors", and U.S. Pat. No. 6,360,888. Other threshold values may be used in conjunction with other offset values to optimize the accuracy of the calculated MSPSR for various types of glucose sensors 12 and sensors used to detect other body characteristics. In fact, many threshold values may be used to select between many offset values. An example using two different threshold values (4.0 mg/dl per nA and 7.0 mg/dl per nA) to select between three different offset values (5.0 mg/dl, 3.0 mg/dl and 0.0 mg/dl) follows:

if SPSR<4.0 mg/dl per nA,offset=5.0 mg/dl;

if 4.0 mg/dl per nA≤SPSR<7.0 mg/dl per nA,offset=3.0 mg/dl; and if SPSR≥7.0 mg/dl per nA,offset=0.0 mg/dl.

In particular embodiments an MSPSR may be compared to a valid sensitivity range to determine whether a newly calculated MSPSR is reasonable. In order to identify potential system problems, a valid MSPSR range of 1.5 mg/dl per nA to 15.0 mg/dl per nA may be employed, for example. However this is merely an example of such a range and claimed subject matter is not limited in this respect. This range may be determined based, at least in part, upon valid glucose sensor sensitivity measurements made in-vitro. MSPSR values outside this range may result in a calibration error alarm (CAL ERROR) to notify the user of a potential problem. Other valid sensitivity ranges may be applied depending on the types of sensors to be calibrated, the range of acceptable sensitivity levels for the various sensor types, the manufacturing consistency expected for the sensors, environmental conditions, how long the sensor has been in use, and/or the like.

Particular embodiments may augment the above described single-point calibration technique using a modified linear regression technique (shown in flow diagram in FIG. 9) if more than one paired calibration data point is available. Paired calibration data points may linearly regressed by a least squares method to calculate a best fit straight line correlated with the paired calibration data points. The slope of the line resulting from the linear regression may be the linear regression sensitivity ratio (LRSR) used as the calibration factor to calibrate the glucose monitor 100.

Figure 10:
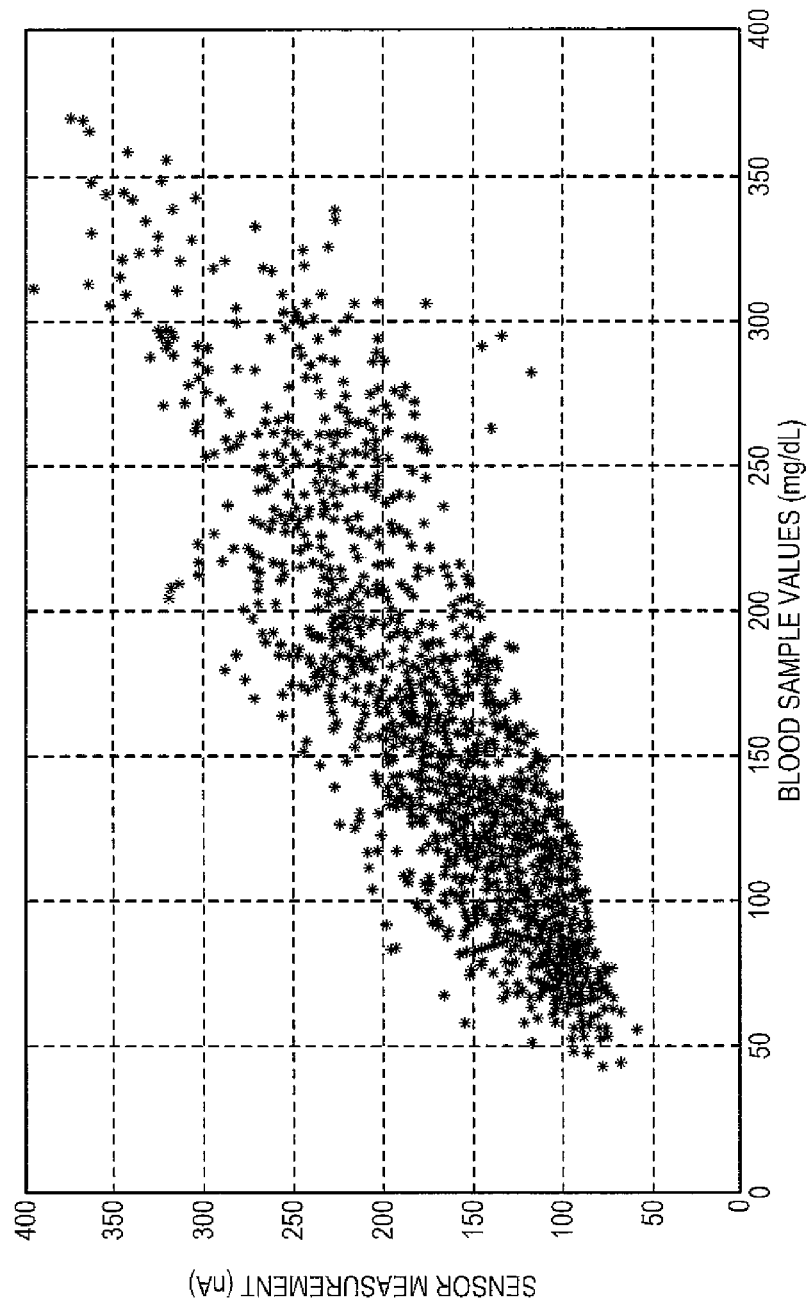
FIG. 10 is a plot of sensor signal values versus reference blood samples according to an embodiment.

Linear and nonlinear least squares regression may apply an assumption that each data point provides equal information about a deterministic part of a total variation in a value or outcome. In such processes a standard deviation of an error associated with a value would be constant for all estimated predictions, for example. In some processes this is not the case. For example, in real-time continuous glucose monitoring using an enzymatic minimally invasive biosensor to estimate plasma glucose concentrations as discussed above, an unequal error distribution may exist. Here, a scatter plot of FIG. 10 illustrates several calibrated glucose sensor points plotted against paired blood glucose reference values throughout a large glycemic range in one particular implementation. It can be observed from the plot that the accuracy of the sensor glucose measurements decreases as the reference blood glucose values increase. Such a decreasing accuracy may be measured as variance and/or standard deviation of an error associated with such measurements that increases with blood glucose concentration and/or paired reference blood glucose reference value. Accordingly, in certain circumstances it may be advantageous not to treat every observation equally, and apply a weighted least squares regression, for example. This may be implemented according to a particular embodiment by giving each point an appropriate weight to control an amount of influence over parameter determination. In doing this, points with less precise influence may be weighted less in computing a linear regression, while points with more influence may be more heavily weighted.

In a particular implementation, paired calibration points, comprising sample values associated with blood-glucose concentration sensor measurements paired with reference measurements at block 852, may be linearly regressed at block 854 to determine an LRSR. As pointed out above, in particular embodiments, such a regression may weight particular pairs and/or sample values according to a degree of certainty associated with the accuracy of such sample values based upon a priori information. Such a linear regression calibration may be computed as follows:

$$LRSR = \frac{\sum_{i=1}^{N} \alpha_i \cdot \beta_i \cdot isig_i \cdot BG_i}{\sum_{i=1}^{N} \alpha_i \cdot \beta_i \cdot isig_i^2}$$

where:

$isig_i$ is a value representing a sensor measurement of a blood glucose concentration for paired calibration point i;

$\alpha_i$ is weighting applied to paired calibration point i based upon the time that the associated sample was obtained;

$BG_i$ is reference sample of a blood glucose concentration for paired calibration point i;

$\beta_i$ is a weighting applied to paired calibration point i based upon a degree of certainty associated with accuracy of $isig_i$ as a measurement of blood glucose concentration; and N is a number of paired calibration data points which are to be linearly regressed.

Accordingly, an estimate of a calibrated blood glucose level may be expressed as follows:

Blood Glucose Level=Valid ISIG*LRSR

In a particular implementation, a paired calibration point may be weighted according to a time associated with when associated sensor measurements and reference values are obtained. Here, for example, pairs based on more recent measurements and reference values may be associated with an error with a smaller variance than pairs based on measurements and reference values obtained in the more distant past. Accordingly, the weight $\alpha_i$ applied to calibration pairs may decrease the more distant in the past such calibration pairs are obtained.

Also, as pointed out above, variances associated with measurement errors in calibrating continuous glucose monitors may not be constant across a dynamic range of blood glucose values. Here, in one particular embodiment, weighting $\beta_i$ may represent an inverse variance weighting. In other words, contribution of each data point may be weighted with the inverse of the variance for that set of blood glucose values. For example, a set of sensor current values were paired (N=90,000 points) and the inverse variance of sensor current calculated for each blood glucose reference value as follows:

$$\beta_i = [\text{var}(isig_i)]^{-1}$$

Here, application of such an inverse variance to calibration pairs to weight samples for linear regression is merely one example of how such calibration pairs may be weighted based upon a decreasing accuracy of sensor measurements, and claimed subject matter is not limited in this respect. Furthermore, it should be understood that a variance or standard deviation are merely examples of how a statistical dispersion of sensor measurement errors may be quantified, and that other metrics may be used. In alternative embodiments, for example, $\beta_i$ may be derived as the inverse of an estimate or approximation of the variance of $isig_i$. Also, as discussed below, appropriate weights may be derived from other functions for determining a weight based, at least in part, on blood glucose reference samples and/or blood glucose concentration.

In this particular implementation, however, $\beta_i$ represents an inverse variance and/or standard deviation of all sensor samples ($isig_i$) measured at a time corresponding to when reference blood glucose sample values i were acquired. In one particular example, inverse variance weights are plotted in FIG. 15c for blood glucose values ranging from 40-400 mg/dL. Again, it should be understood, however, that the use of an inverse variance is merely one example of how calibration pairs may be weighted based upon a degree of certainty associated with accuracy of sensor measurements and claimed subject matter is not limited in this respect.

Figure 11:
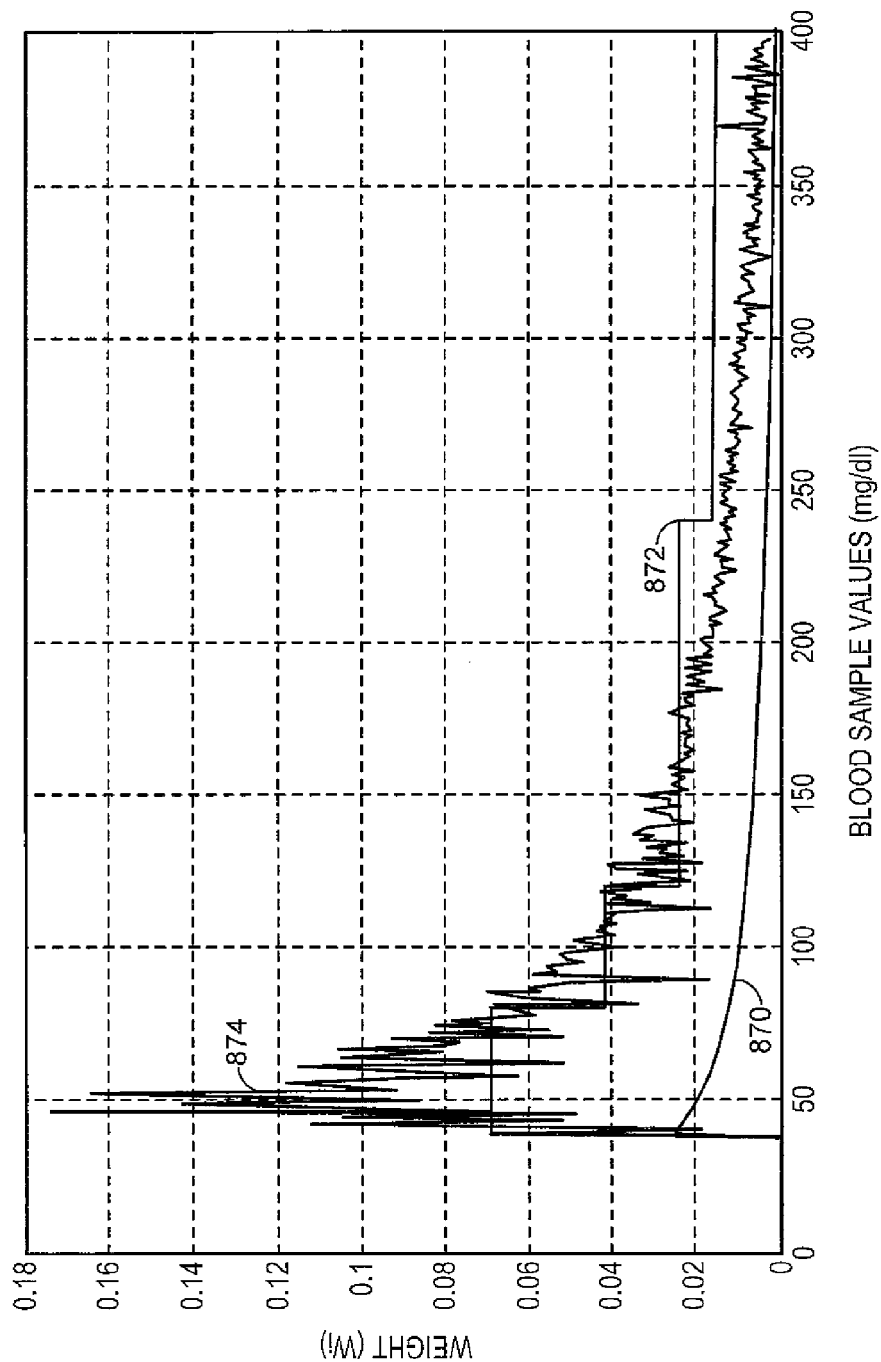
FIG. 11 is a plot of an inverse variance of sensor signal values versus blood glucose concentration according to an embodiment.
Figure 12:
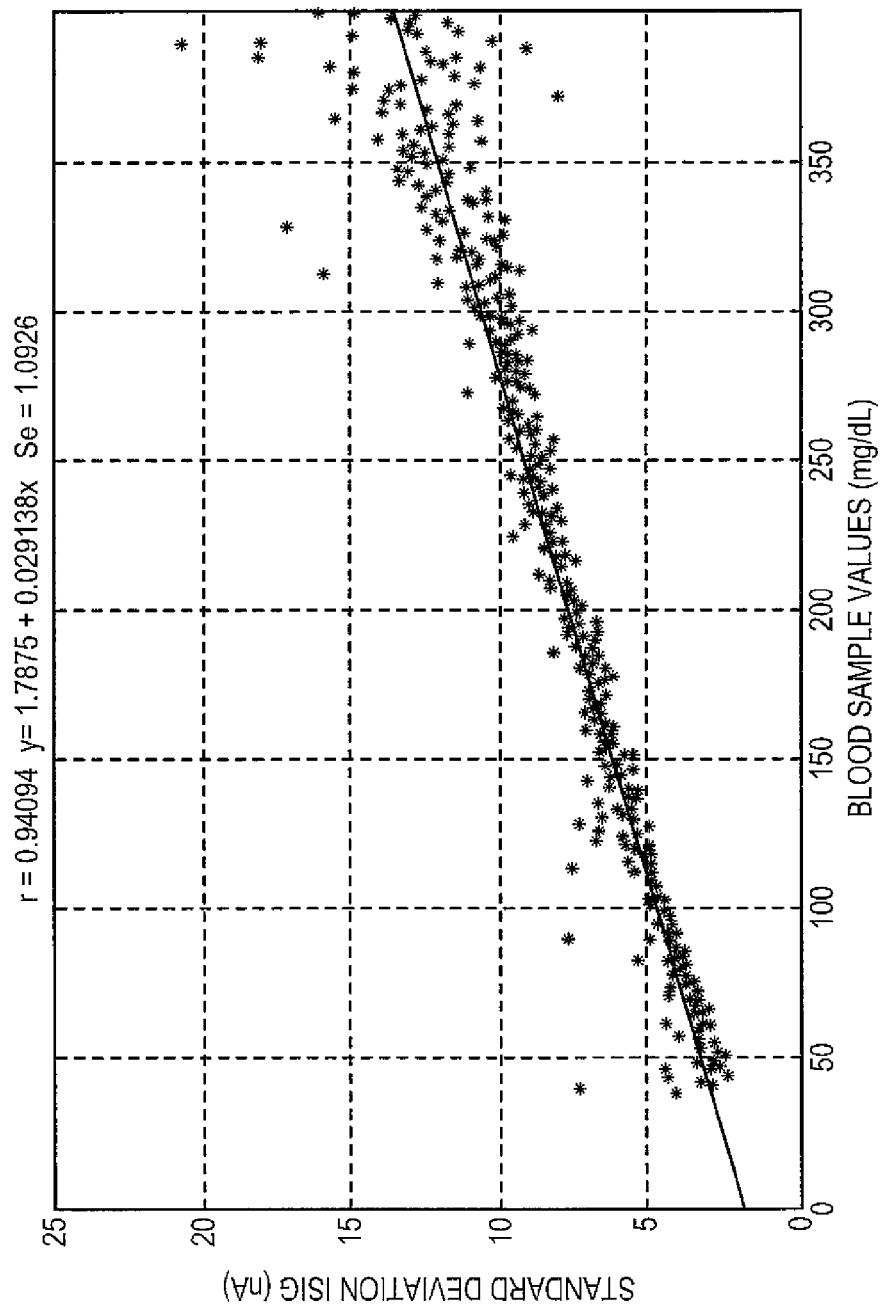
FIG. 12 is a plot illustrating a linear best fit of a standard deviation of sensor measurements versus blood glucose concentration according to an embodiment.

Alternatively, weights (for application to calibration pairs in a linear regression) may be obtained from a function based on an inverse variance weights. Here, use of such a function may provide a high quality estimate that removes noise present in the inverse variance weights arising from sources such as, for example, variability between blood-glucose and a blood glucose monitor. This may be illustrated in FIG. 11 where a best line fit is produced by regressing the square root of the variance or standard deviation. For the particular example of sensor measurement samples shown in FIG. 10, weights may be determined according to the corresponding function derived from such a best line fit as follows:

$$w_i = \frac{1}{(1.787 + 0.0291 \cdot i)^2}$$

Figure 13:
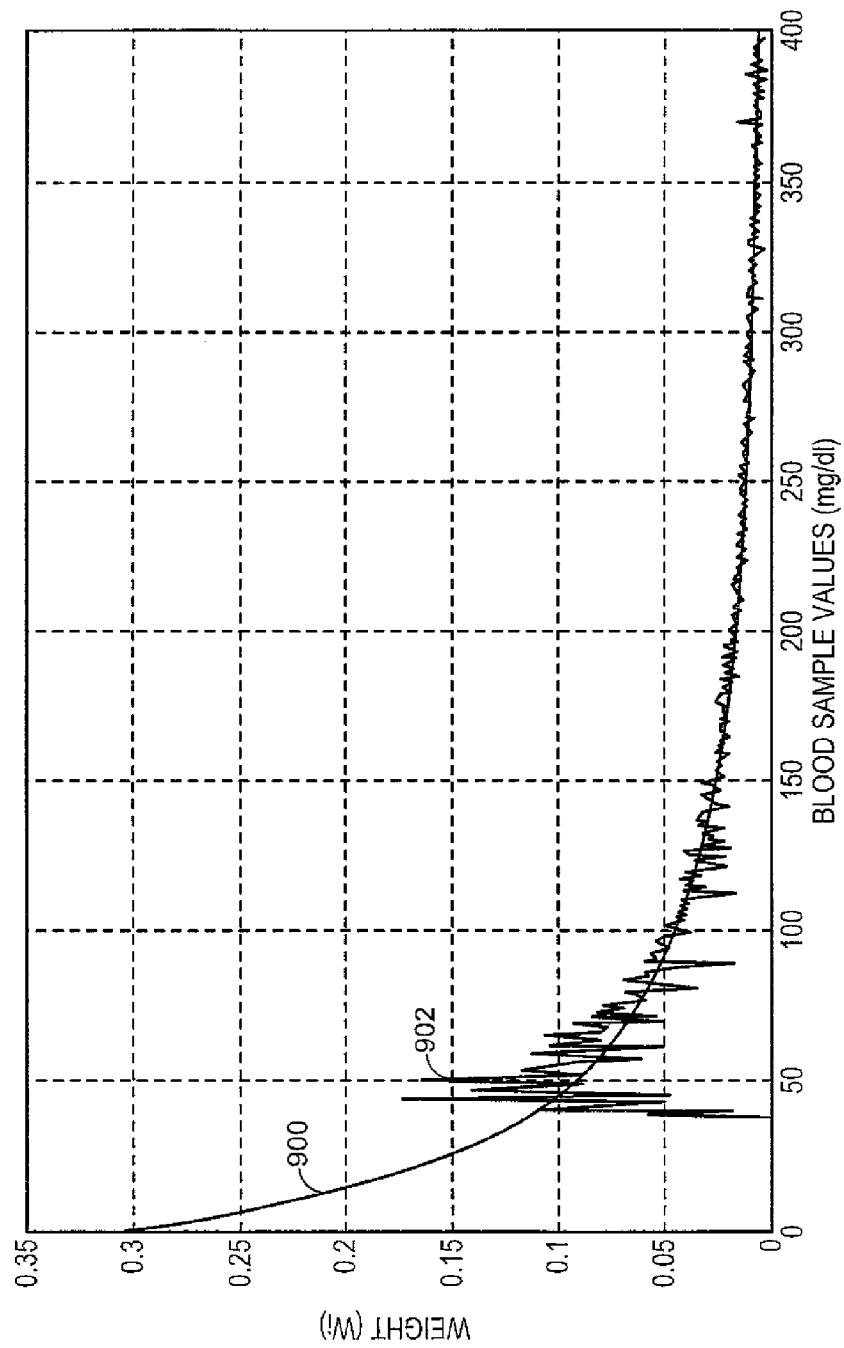
FIG. 13 is a plot of a function for obtaining weights to be applied to sensor sample values according to an embodiment.

FIG. 13 shows a plot of inverse variance $\beta_i$ and function derived from such a best line fit of variance/standard deviation as a function of ISIG weights $w_i$ over a range of blood glucose concentration range from 0 to 400 mg/dl. An inverse variance is plotted as 902 while a weighting function is plotted as 900. As can be observed, the weighting function 900 removes noise in the inverse variance to provide a weighting function to be applied to calibration pairs that is a decreasing function of blood glucose concentration and/or associated blood sample reference values associated with such calibration pairs.

It should be observed that this particular linear regression uses a fixed intercept of zero. In other words, if the Valid ISIG is 0 the blood glucose value is 0. Accordingly, this particular linear regression method estimates only one regression parameter, the slope. In alternative embodiments, other linear regression methods may be used that estimate additional regression parameters such as an offset value.

At block 856, particular embodiments may select an offset value for use in calculating a modified linear regression calibration. The purpose of such an offset value, as described above for the single-point calibration, is to compensate for an observation that more sensitive glucose sensors 12 may have a less linear performance at very high blood glucose levels. If an LRSR for a particular glucose sensor 12, as calculated in the linear regression calibration expression above, is less than a sensitivity threshold value, then a modified linear regression sensitivity ratio (MLRSR) may be calculated using an offset value included in a modified linear regression calibration expression. In one particular embodiment, for example, such a sensitivity threshold may be 7.0 mg/dl per nA. Here, if an initial calculation of an LRSR is less than 7.0 mg/dl per nA, an offset value of 3.0 mg/dl may be used to calculate an MLRSR. If an initial calculation of LRSR yields a value of 7.0 mg/dl per nA or greater, an offset value of 0.0 mg/dl may be used. Thus, MLRSR may be calculated at block 858 using the selected offset value in the modified linear regression calibration according to the following expression:

$$MLRSR = \frac{\sum_{i=1}^{N} \alpha_i \cdot \beta_i \cdot [isig_i - \text{offset}] BG_i}{\sum_{i=1}^{N} \alpha_i \cdot \beta_i \cdot [isig_i - \text{offset}]^2}$$

Accordingly, a calculated blood glucose level may be estimated at block 860 as follows:

Blood Glucose Level=(Valid ISIG−offset)*MLRSR

Just as in the case of single-point calibration techniques described above, other threshold values may be used at block 856 in conjunction with other offset values in the modified linear regression calibration equation to optimize the accuracy of the calculated MLRSR for various types of glucose sensors 12 and other characteristic sensors.

In particular embodiments, a newly calculated MLRSR may be compared to a valid sensitivity range to determine whether the newly calculated MLRSR is reasonable. To identify potential system problems, a valid MLRSR range of 2.0 mg/dl per nA to 10.0 mg/dl per nA may be employed. MLRSR values outside this range may result in a calibration error alarm (CAL ERROR) to notify a user of a potential problem. As described above for the single-point calibration techniques, other valid sensitivity ranges may be applied.

In particular embodiments, glucose monitor data (e.g., paired calibration data points as discussed above) may be linearly regressed over a 24 hour period (or window), and new sensitivity ratios may be used for each 24 hour time period. In other embodiments, a time period may be reduced to only a few hours or enlarged to cover the entire monitoring period with the glucose sensor (e.g., several days—or even weeks with implanted sensors). In further embodiments, such a time window may be fixed at a predetermined size, such as 24 hours, 12 hours, 6 hours, and/or the like, and the window is moved along over the operational life of the sensor.

In particular embodiments, paired calibration data points from measurements taken before the last calibration may be used to calculate a new sensitivity ratio. For example, to calibrate the glucose monitor every 6 hours, a paired calibration data point may be established every 6 hours. A linear regression technique described above may be executed using four paired calibration data points, the most recently acquired point and points obtained from six, twelve and eighteen hours before. Alternatively, a number of paired calibration data points used in the calibration may be as few as one or as large as the total number of paired calibration data points collected since the glucose sensor was installed. In alternative embodiments, a number of paired calibration data points used in a calibration computation may grow or shrink during the life of the glucose sensor due to glucose sensor anomalies.

In still other embodiments, decay characteristics of glucose sensor 12 over time may be factored into the equation to account for known degradation characteristics of glucose sensor 12 due to site characteristics, enzyme depletion, body movement, and/or the like. Considering these additional parameters in the calibration equation may more accurately tailor calibration computations used by the glucose monitor 100 or post processor 200. In particular embodiments, other parameters may be measured along with the blood glucose such as, temperature, pH, salinity, and/or the like. These other parameters may be used to calibrate the glucose sensor using non-linear techniques.

Figure 14:
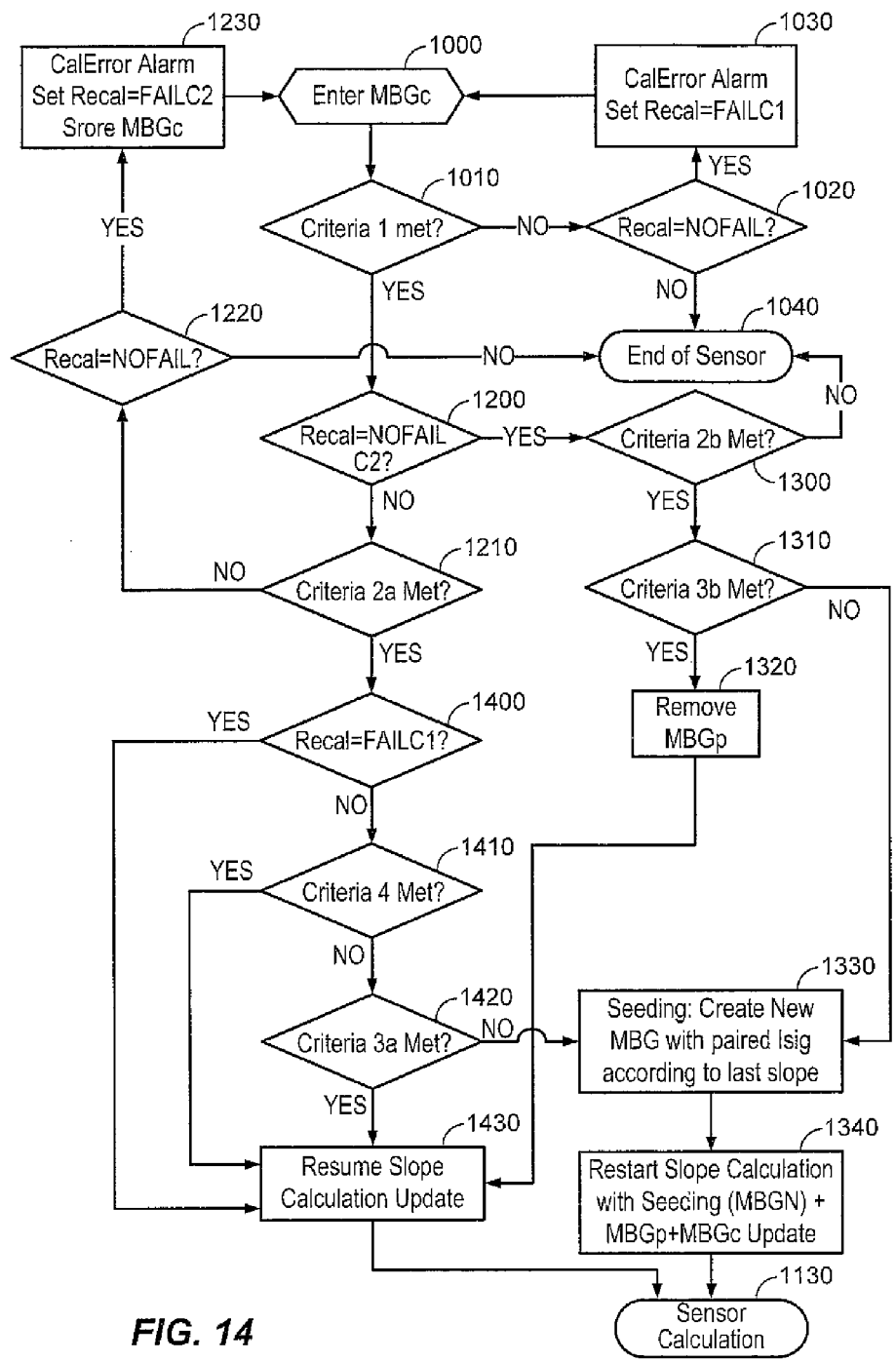
FIG. 14 is a flowchart of a self-adjusting technique deriving a linear portion of a function in accordance with an embodiment.

In a particular embodiment, real-time calibration adjustment can be performed to account for changes in the sensor sensitivity during the lifespan of the glucose sensor 12 and to detect when a sensor fails. FIG. 14 (in conjunction with FIGS. 15-18) describes the logic of a self-adjusting calibration technique to adjust the calibration formula or detect a sensor failure in accordance with one particular implementation.

At block 1000, a user may obtain a blood glucose reference from a common glucose meter, or another blood glucose measuring device, and immediately enter the blood glucose reference reading into glucose monitor 100. For every such meter blood glucose entry, an instantaneous calibration check may be performed and compared to an expected range of the value of the calibration check, as in block 1010. In particular embodiments, a Calibration Factor current is calculated (e.g., CFc=Meter BG/current ISIG value) to determine if the CFc (Calibration Factor current) ratio is between 1.5 to 12.0 mg/dl per nA ("Criteria 1"), one criterion for an accurate ISIG value in a particular implementation. If data is outside this range, raising a likelihood of a sensor failure or incorrect determination/entry of a meter BG value, a Cal Error alarm may be triggered at block 1030 and the Recalibration Variable (Recal), which is originally set at NOFAIL may be changed to FAILC1. At this point, another blood glucose reference reading may be requested and entered into the glucose monitor 100 to determine whether there was indeed a sensor failure or the Meter Blood Glucose value was incorrectly inputted. The previous Metered Blood Glucose value that generated the error can be thrown out completely. If Criteria 1 is again not satisfied at block 1010, an end of the sensor life message may be generated at block 1040 since then the Recal variable would be recognized as FAILC1 at block 1020. However, if Criteria 1 is met at block 1010, then block 1200 may determine whether the Recal variable is not equal to FAILC2. Here, the Recal variable is set to FAILC2 only if Criteria 2a is not met, which is discussed below. Given that the Recal variable at this point may only be set to a NOFAIL or FAILC1, logic proceeds to block 1210.

Block 1210, a check is performed to determine whether an existing calibration slope estimation (Previous Estimated Slope or PES) is much different from the CFc performed using a new meter blood glucose value. A significant difference may indicate a sensor failure, for example. In a particular embodiment, a difference between a previous estimated slope (PBS) and a CFc in terms of percentage (threshold 1) and mg/dl (threshold 2) may be performed. Thresholds 1 and 2 may be set depending on particular sensor characteristics. In a particular implementation, an example of checking such changes between the PES and CFc may be performed as follows:

$$|1-PES/CFc|*100 > \text{threshold 1; and}$$

$$|CFc-PES|*isig > \text{threshold 2.}$$

If threshold 1 and/or threshold 2 are exceeded according to the above expressions (collectively "Criteria 2a"), then depending on the Recal variable (at block 1220), either trigger an end of sensor message may be triggered at block 1040 (if the Recal variable is equal to FAILC1 or FAILC2 at block 1220) or a Cal Error alarm may be generated at block 1230 (if the Recal variable is equal to NOFAIL at block 1220). Here, if a Cal Error alarm is generated at block 1230, the Recal variable may be set to FAILC2, the current meter blood glucose reading will be stored as MBGp (Meter Blood Glucose previous), and another blood glucose reference is requested and entered into the glucose monitor 100 (as MBGc) at block 1000. By requesting a new meter blood glucose reading, a comparison can be made between the last meter blood glucose reading stored at block 1230, and the new meter blood glucose reading entered at block 1000 may be used to determine whether there was a sensor failure. The logic follows the same paths as described above after block 1000 until the logic reaches block 1200. At block 1200, since Recal variable is now set to FAILC2 at block 1230, a difference between the previous calibration check (CFp), which generated the FAILC2 alert, and the CFc is performed at block 1300. In particular implementations, the difference between the previous calibration check and the current calibration check in terms of percentage (threshold 1) and mg/dl (threshold 2) may also be performed. In addition, a check is performed to determine whether there has been a directional change between the CFp and CFc (collectively "criteria 2b"). An example of criteria 2b may be expressed as follows:

$$|1-CFp/CFc|*100 > \text{threshold 1;}$$

$$|CFc-CFp|*Isig > \text{threshold 2; and}$$

$$(CFp-PES)*(CFc-CFp) > 0.$$

If the percentage and absolute difference exceeds threshold 1 and threshold 2, and there is no directional change in the slope with the second blood glucose meter reading, then an end of sensor message will be triggered at block 1040. If criteria 2b is met, then the logic proceeds to block 1310. At block 1310, the logic then determines whether the difference between the previous value and the current value was due to a change in sensitivity of the sensor or whether the reading is merely noise. In the preferred embodiment, the determination of change in sensitivity versus noise is made by using Criteria 3b. Criteria 3b compares the difference between (the PES and CFc) and (the CFp versus the CFc) at block 1420. For example:

$$|PES-CFc|<|CFp-CFc|$$

Figure 15:
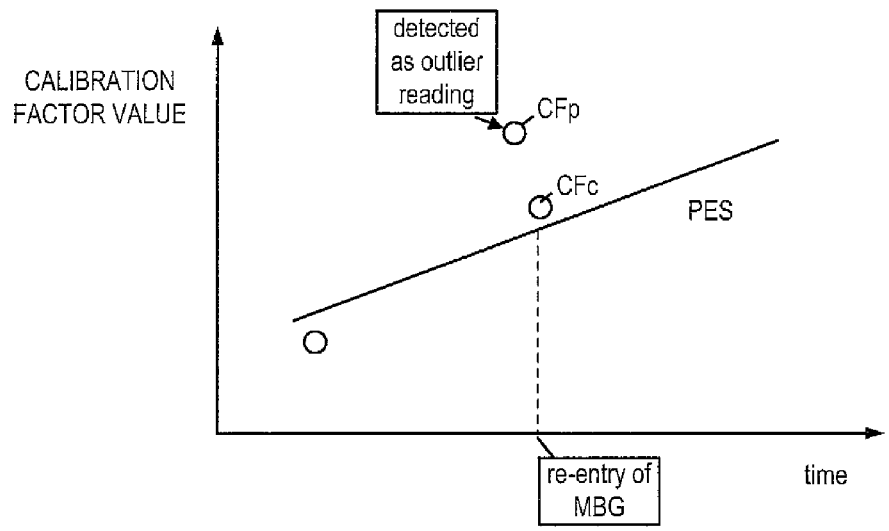
FIGS. 15 and 16 are charts illustrating an example of a self-adjusting calibration technique according to an embodiment.

As illustrated in FIG. 15, if a difference between PES and CFc is less than a difference between CFp and CFc, criteria 3b will be met, indicating that the previous CFp is an outlier reading (e.g., an anomaly). Then, the MBGp (Meter Blood Glucose previous) is removed at block 1320 and only the MBGc paired with a valid ISIG is used in the slope calculation, which is resumed at block 1430 and applied in interpreting the sensor readings at block 1130.

Figure 16:
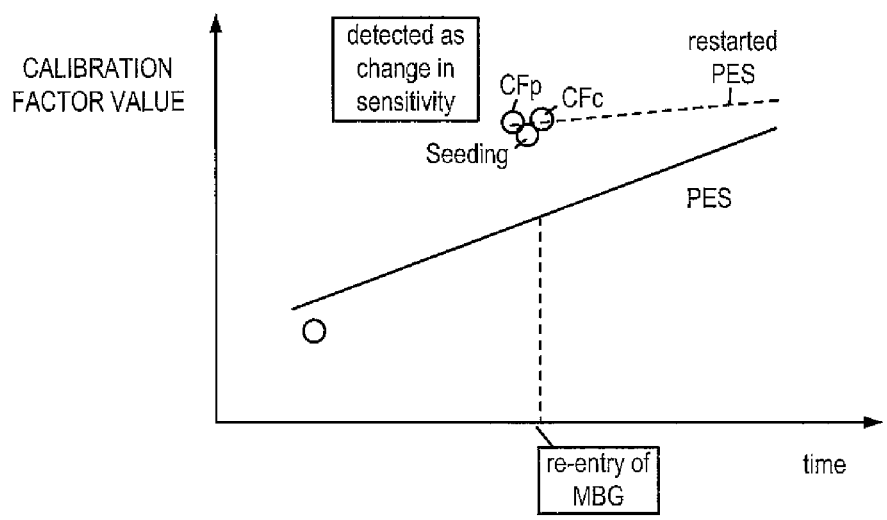

As illustrated in FIG. 16, if criteria 3b shows that a difference between the PES and CFc is greater than a difference between CFp and CFc, criteria 3b would not be met, indicating a change in sensor sensitivity. A slope calculation may then be fine-tuned by creating a new (artificial) meter blood glucose value (MBGN) with a paired ISIG according to the last slope (Seeding) at block 1330. Using the new paired MBG (MBGN) with the paired MBGp and MBGc, the slope calculation may be restarted (or reset) at block 1340, as seen in FIG. 16. Sensor calculation may then be performed using a new slope calculation at block 1130. By resetting a slope calculation, such a slope calculation can thus be modified automatically to account for changes in sensor sensitivity.

Continuing the logic from block 1210, if the percentage and/or absolute difference between the PES and CFc is within threshold 1 and/or threshold 2 at block 1210, indicating a valid calibration, the Recal variable is again checked at block 1400. If the Recal variable is equal to FAILC1 (indicating that the meter BG was checked twice), any fine-tuning determination may be skipped and the MBGc may be paired with a valid ISIG for use in updating a slope calculation at block 1430 and applied in interpreting sensor readings at block 1130. If the Recal Variable is not equal to FAILC1, then the logic may decide whether fine-tuning the slope calculation is needed at blocks 1410 and 1420. In particular embodiments, a decision to fine-tune may be first made by comparing a percentage and/or absolute difference between the PES and CFc (as done in block 1210) with a threshold 3 and/or a threshold 4 ("Criteria 4") at block 1410 as follows:

$$|1-PES/CFc|*100<threshold\ 3;\ and$$

$$|CFc-PES|*isig<threshold\ 4.$$

Again, threshold 3 and 4 may be determined based, at least in part, on particular sensor characteristics. If a percentage and/or absolute difference between PES and CFc is less than threshold 3 and/or threshold 4 at block 1410 (i.e. Criteria 4 met), then the slope calculation can simply be updated with the new MBGc and paired ISIG value at block 1430, and applied in interpreting the sensor readings at block 1130.

On the other hand, if the Criteria 4 is not met at block 1410, block 1420 may determine whether the difference between the expected value and the current value was due to a change in sensitivity of the sensor or whether the reading is merely noise. In one particular implementation, such a determination of change in sensitivity versus noise may be made by using Criteria 3a. Here, criteria 3a CFc and a CFp at block 1420 as follows:

$$|PES-CFp|<|CFc-CFp|$$

Figure 17:
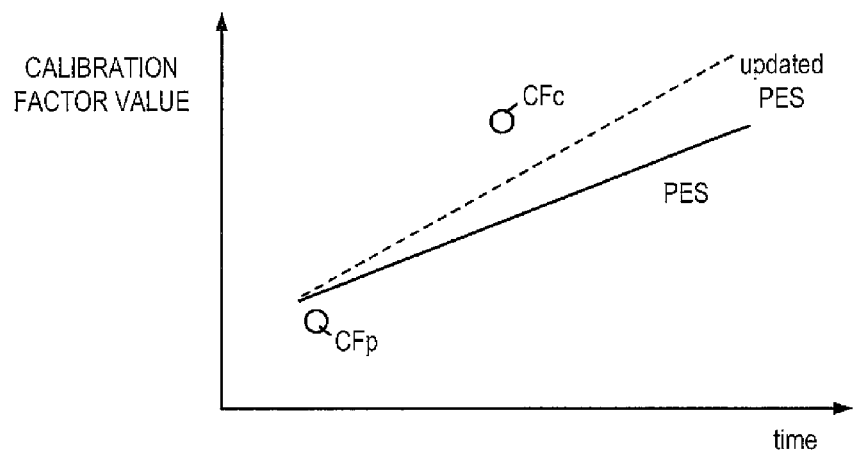
FIGS. 17 and 18 are further charts illustrating an example of a self-adjusting calibration technique according to an embodiment.

As seen in FIG. 17, if the difference between a PES and CFp is less than a difference between CFc and the CFp, criteria 3a may be met, indicating that an error between predicted and actual values for the CFc was due to noise in previous calibrations or beginning of a change in sensor sensitivity which may be picked up in a subsequent calibration cycle. Slope calculation may then be updated with a new paired blood glucose entry (MBGc) at block 1430 and applied in interpreting sensor readings at block 1130.

Figure 18:
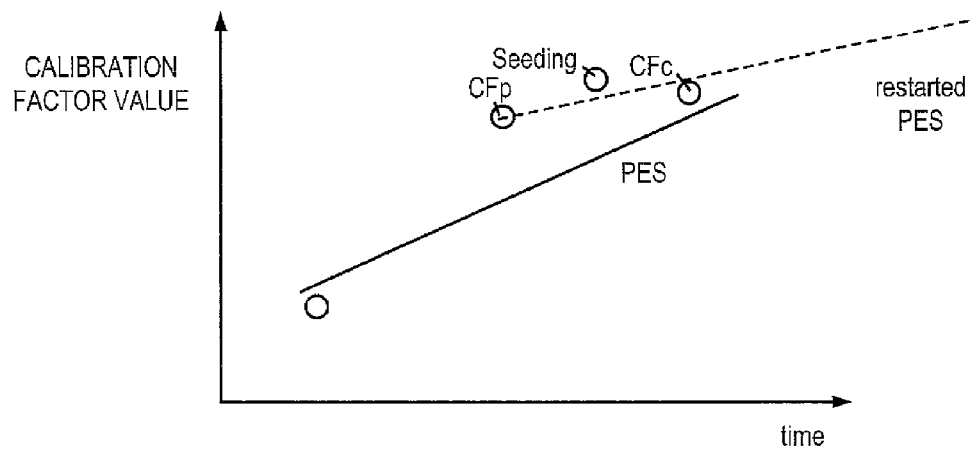

As seen in FIG. 18, if criteria 3a shows that a difference between the PES and the previous valid calibration check is greater than a difference between the previous valid CFp and the CFc, criteria 3b would not be met, indicating a change in the sensor sensitivity and fine tuning is performed. Here, such fine tuning may be performed if two MBG entries in succession indicate a change in slope. Slope calculation may be fine-tuned by creating a new (artificial) MBGN with a paired ISIG according to the last slope (Seeding) at block 1330. Using such a new paired MBGN with the paired MBGp and MBGc, a slope calculation may be restarted (or reset) at block 1340, as seen in FIG. 18. The sensor calculation may then be performed using the new slope calculation at block 1130. Again, by resetting the slope calculation, the slope calculation can thus be modified automatically to account for changes in sensor sensitivity.

Although the above description described the primary calibration techniques in particular embodiments, many modifications can be made to the above described calibration techniques without deviating from claimed subject matter. For example, in alternative embodiments, a calibration factor may be calculated by first using a single-point technique to calculate an MSPSR for each paired calibration data point, and then averaging them together, either unweighted or weighted by temporal order of by elapsed time.

As discussed above, particular embodiments described herein utilize a least squares linear regression computation to calibrate the glucose monitor 100 and/or analyze sensor data using post-processor 200, for example. However, alternative embodiments may utilize a multiple component linear regression computation with more variables than just the paired calibration data points discussed above, to account for additional calibration effecting parameters, such as environment, an individual user's characteristics, sensor lifetime, manufacturing characteristics (such as lot characteristics), deoxidization, enzyme concentration fluctuation and/or degradation, power supply variations, and/or the like.

In particular implementations, after a first calibration is performed on a particular glucose sensor 12, subsequent calibrations may employ a weighted average using a sensitivity ratio (SPSR, MSPSR, LRSR, or MLRSR) calculated from data collected since the last calibration, and previous sensitivity ratios calculated for previous calibrations. Here, an initial sensitivity ratio (SR1) may be calculated immediately after initialization/stabilization using a paired calibration data point, and used by glucose monitor 100 or post processor 200 until a second sensitivity ratio (SR2) is calculated. Here, second sensitivity ratio SR2 may comprise an average of SR1 and the sensitivity ratio as calculated using the paired cali bration data points since the initial calibration (SRday1) as follows:

$$SR2 = \frac{SR1 + SRday1}{2}$$

The third sensitivity ratio (SR3) is an average of SR2 and the sensitivity ratio as calculated using the paired calibration data points since the second calibration (SRday2). The equation is as follows:

$$SR3 = \frac{SR2 + SRday2}{2}$$

Sensitivity ratios for successive days may be similarly determined as follows:

$$SR_n = \frac{SR_{(n-1)} + SRday_{(n-1)}}{2},$$

where:
$SR_n$ is the new sensitivity ratio calculated at the beginning of time period, n, using data from time period (n−1), to be used by glucose monitor 100, to convert Valid ISIGs measurement values to blood glucose readings throughout time period n;
$SR_{(n-1)}$ is a previous sensitivity ratio calculated at the beginning of time period n−1, using data from time period n−2; and
$SRday_{(n-1)}$ is the sensitivity ratio calculated using paired calibration data points collected since the last calibration.

Alternatively, previous sensitivity ratios may be ignored and SR may be calculated using only the paired calibration data points since the last calibration. In another alternative, all previous SRs may be averaged with the latest SR calculated using only the paired calibration data points since the last calibration. In other implementations, the paired calibration data points are used to establish an equation for a curve representing SR over time. The curve may then used to extrapolate SR to be used until the next paired calibration data point is entered.

In embodiments that use a post processor 200 to evaluate a sensitivity ratio, such a sensitivity ratio may be calculated using paired calibration data points over a period of time since a last calibration, and is not averaged with previous sensitivity ratios. A sensitivity ratio determined for a period of time may then be applied to the same period of time over which the paired calibration data points were collected. This may result in a more accurate than the real-time case described above for the glucose monitor 100 because, in the real-time case, sensitivity ratios from a previous time period must be used to calculate the blood glucose level in the present time period. If the sensitivity ratio has changed over time, estimation of blood glucose using an old sensitivity ratio may introduce an error.

In particular embodiments, once calibration is complete, Valid ISIG values may be converted to blood glucose readings based on a particular version of the sensitivity ratio, and the resulting blood glucose readings are compared to an out-of-range limit. If such a resulting calculated blood glucose level is greater than a maximum out-of-range limit of 200 mg/dl (or equivalently 3600 mmol/l), the out-of-range alarm is activated. This is a calibration cancellation event, therefore, ISIG values are no longer valid once this alarm is activated. Blood glucose readings are either not calculated, or at least not considered reliable, until the glucose monitor 100 or post processor 200 is re-calibrated. The user may be notified of the alarm and that re-calibration is needed.

In alternative embodiments, higher or lower maximum out-of-range limits may be used depending on the sensor characteristics, the characteristic being measured, the user's body characteristics, and the like. In particular implementations, a minimum out-of-range limit may be used or both a maximum and a minimum out-of-range limits may be used. In other particular embodiments, such out-of-range limits may not cause blood glucose readings to become invalid and/or re-calibration is not required; however, an alarm could still be provided. In additional particular embodiments, an alarm may be activated in response to two or more ISIG values exceeding an out-of-range limit. ISIG values that are out-of-range may be omitted from display.

In alternative embodiments, calibration may be conducted by injecting a fluid containing a known value of glucose into the site around the glucose sensor set 10, followed by sending one or more glucose sensor readings to glucose monitor 100. The readings may then be processed (filtered, smoothed, clipped, averaged, and/or the like) and used along with the known glucose value to calculate the SR for the glucose sensor 12. Particular alternative embodiments may use a glucose sensor set of the type described in U.S. Pat. No. 5,951, 521 entitled "A Subcutaneous Implantable Sensor Set Having the Capability To Remove Or Deliver Fluids To An Insertion Site".

In other alternative embodiments, glucose sensor 12 may be supplied with a vessel containing a solution with a known glucose concentration to be used as a reference, and glucose sensor 12 is immersed into the reference glucose solution during calibration. Glucose sensor 12 may be shipped in the reference glucose solution, for example. As described above, glucose sensor readings may be used to calculate a sensitivity ratio given a known (or independently measured) glucose concentration of the solution.

In another alternative embodiment, glucose sensors 12 may be calibrated during a manufacturing process. Sensors from the same manufacturing lot have similar properties may be calibrated using a sampling of glucose sensors 12 from the population and a solution with a known glucose concentration. A sensitivity ratio is provided with the glucose sensor 12 and is entered into glucose monitor 100 or post processor 200 by the user or another individual.

In addition, although the particular process of FIG. 14 includes specific operations occurring in a particular order, in alternative embodiments, certain of these operations may be performed in a different order, modified, or removed while not deviating from claimed subject matter. Moreover, other operations may be added to and/or combined with the above described process without deviating from claimed subject matter.

Unless specifically stated otherwise, as apparent from the following discussion, it is appreciated that throughout this specification discussions utilizing terms such as "processing", "computing", "calculating", "determining", "estimating", "selecting", "weighting", "identifying", "obtaining", "representing", "receiving", "transmitting", "storing", "analyzing", "creating", "contracting", "associating", "updating", or the like refer to the actions or processes that may be performed by a computing platform, such as a computer or a similar electronic computing device, that manipulates or transforms data represented as physical, electronic or magnetic quantities or other physical quantities within the computing platform's processors, memories, registers, or other information storage, transmission, reception or display devices. Accordingly, a computing platform refers to a system or a device that includes the ability to process or store data in the form of signals. Thus, a computing platform, in this context, may comprise hardware, software, firmware or any combinations thereof. Further, unless specifically stated otherwise, a process as described herein, with reference to flow diagrams or otherwise, may also be executed or controlled, in whole or in part, by a computing platform.

It should be noted that, although aspects of the above system, method, or process have been described in a particular order, the specific order is merely an example of a process and claimed subject matter is of course not limited to the order described. It should also be noted that the systems, methods, and processes described herein, may be capable of being performed by one or more computing platforms. In addition, the methods or processes described herein may be capable of being stored on a storage medium as one or more machine readable instructions, that if executed may enable a computing platform to perform one or more actions. "Storage medium" as referred to herein relates to media capable of storing information or instructions which may be operated on, or executed by, by one or more machines. For example, a storage medium may comprise one or more storage devices for storing machine-readable instructions or information. Such storage devices may comprise any one of several media types including, for example, magnetic, optical or semiconductor storage media. For further example, one or more computing platforms may be adapted to perform one or more of the processed or methods in accordance with claimed subject matter, such as the methods or processes described herein. However, these are merely examples relating to a storage medium and a computing platform and claimed subject matter is not limited in these respects.

The terms, "and," and "or" as used herein may include a variety of meanings that will depend at least in part upon the context in which it is used. Typically, "or" if used to associate a list, such as A, B or C, is intended to mean A, B, and C, here used in the inclusive sense, as well as A, B or C, here used in the exclusive sense. Reference throughout this specification to "one example" or "an example" means that a particular feature, structure, or characteristic described in connection with the example is included in at least one example of claimed subject matter. Thus, the appearances of the phrase "in one example" or "an example" in various places throughout this specification are not necessarily all referring to the same example. Furthermore, the particular features, structures, or characteristics may be combined in one or more examples. Examples described herein may include machines, devices, engines, or apparatuses that operate using digital signals. Such signals may comprise electronic signals, optical signals, electromagnetic signals, or any form of energy that provides information between locations.

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all aspects falling within the scope of appended claims, and equivalents thereof.

What is claimed is:

1. A method comprising:
   obtaining a sequence of blood glucose reference measurements from a patient;
   deriving, using an electronic computing device, a non-linear mapping between sensor signal values (ISIG) and blood glucose concentration in said patient to calibrate a glucose monitor for observing glucose characteristics of said patient, said non-linear mapping based, at least in part, on temporal pairings of at least some of said blood glucose reference measurements with said sensor signal values, wherein said deriving said non-linear mapping further comprises deriving a piece-wise function that maps sensor signal values to blood-glucose concentration, the piece-wise function comprising at least one linear portion and at least one non-linear portion, the at least one non-linear portion being derived at least in part by determining coefficients e, f, and g corresponding to the following function:

$$\text{blood-glucose reference measurement} = (ISIG++e)^f;$$
   and with said electronic computing device, using, at least in part, said determined coefficients e, f and g in calibrating subsequent sensor signal values received by said glucose monitor to provide said patient one or more estimated blood glucose levels corresponding to said subsequent sensor signal values.

2. The method of claim 1, and further comprising determining coefficients e, f, and g based, at least in part, on said temporal pairings.

3. The method of claim 1, and further comprising, for values in said non-linear portion, obtaining a measurement of blood glucose concentration by applying an offset to a function defining said linear portion.

4. An apparatus comprising:
   a sensor to generate signal values (ISIG) responsive to a blood glucose concentration in a body; and
   a special purpose computing apparatus programmed to:
     obtain a sequence of blood glucose reference measurements taken from said body; and
   derive a non-linear mapping between said signal values and blood glucose concentration in said body to calibrate a glucose monitor for observing blood glucose characteristics in said body based, at least in part, on temporal pairings of at least some of said blood glucose reference measurements with said signal values, wherein said non-linear mapping is derived by deriving a piece-wise function that maps sensor signal values to blood glucose concentration, the piece-wise function comprising at least one linear portion and at least one non-linear portion, the at least one non-linear portion being derived at least in part by a determination of coefficients e, f, and g corresponding to the following function:

$$\text{blood-glucose reference measurement} = (ISIG+e)^f + g;$$
   and use, at least in part, said determined coefficients e, f and g in calibrating subsequent signal values received by said glucose monitor to provide one or more estimated blood glucose levels corresponding to said subsequent signal values.

5. The apparatus of claim 4, wherein said special purpose computing apparatus is further programmed to obtain a measurement of blood glucose concentration by applying an offset to a function defining said linear portion for values in said non-linear portion.

6. The apparatus of claim 4, wherein said determination of coefficients e, f, and g is based, at least in part, on said temporal pairings.

7. An article comprising:
a non-transitory storage medium having machine-readable instructions stored thereon which are executable by a special purpose computing apparatus to:
obtain a sequence of blood glucose reference measurements taken from a body; and
derive a non-linear mapping between sensor signal values (ISIG) and blood glucose concentration in said body to calibrate a glucose monitor for observing blood glucose characteristics in said body based, at least in part, on temporal pairings of at least some of said blood glucose reference measurements with said sensor signal values, wherein said non-linear mapping is derived by deriving a piece-wise function that maps sensor signal values to blood-glucose concentration, the piece-wise function comprising at least one linear portion and at least one non-linear portion, wherein the at least one non-linear portion is derived at least in part by a determination of parameters e, f, and g corresponding to the following function:

blood-glucose reference measurement=$(ISIG+e)^f+g$;
and use, at least in part, said determined coefficients e, f, and g to calibrate subsequent sensor signal values received by said glucose monitor to provide one or more estimated blood glucose levels corresponding to said subsequent sensor signal values.

8. The article of claim 7, wherein said instructions are further executable by said special purpose computing apparatus to obtain a measurement of blood glucose concentration by applying an offset to a function defining said linear portion for values in said non-linear portion.

9. The article of claim 7, wherein a determination of parameters e, f, and g is based, at least in part, on said temporal pairings.

10. An apparatus comprising:
means for obtaining a sequence of blood glucose reference measurements from a body; and
means for deriving a non-linear mapping between sensor signal values (ISIG) and blood glucose concentration in said body to calibrate a glucose monitor for observation of blood glucose characteristics in said body based, at least in part, on temporal pairings of at least some of said blood glucose reference measurements with said sensor signal values, wherein said means for deriving said non-linear mapping further comprises means for deriving a piece-wise function that maps sensor signal values to blood-glucose concentration, the piece-wise function comprising at least one linear portion and at least one non-linear portion, wherein the at least one non-linear portion is derived at least in part by a determination of parameters e, f, and g corresponding to the following function:

blood-glucose reference measurement=$(ISIG+e)^f+g$;
and means for using, at least in part, said determined coefficients e, f, and g to calibrate subsequent sensor signal values received by said glucose monitor to provide one or more estimated blood glucose levels corresponding to said subsequent sensor signal values.

11. The apparatus of claim 10, and further comprising means for determining parameters of said exponential expression based, at least in part, on said temporal pairings.

12. The apparatus of claim 10, and further comprising, for values in said non-linear portion, means for obtaining a measurement of blood glucose concentration by applying an offset to a function defining said linear portion.

* * * * *